(12) United States Patent
Agüeros Bazo et al.

(10) Patent No.: US 10,894,006 B2
(45) Date of Patent: Jan. 19, 2021

(54) NANOPARTICLES FOR THE ENCAPSULATION OF COMPOUNDS, PREPARATION THEREOF AND USE OF SAME

(75) Inventors: Maite Agüeros Bazo, Pamplona-Navarra (ES); Irene Esparza Catalán, Pamplona-Navarra (ES); Carolina González Ferrero, San Adrián-Navarra (ES); Carlos Javier González Navarro, San Adrián-Navarra (ES); Juan Manuel Irache Garreta, Pamplona-Navarra (ES); Ana Romo Hualde, San Adrián-Navarra (ES)

(73) Assignees: CENTRO NACIONAL DE TECNOLOGÍA Y SEGURIDAD ALIMENTARIA, LABORATORIO DEL EBRO, San Adrián-Navarra (ES); UNIVERSIDAD DE NAVARRA, Pamplona-Navarra (ES)

(*) Notice: Subject to any disclaimer, the term of this patent is extended or adjusted under 35 U.S.C. 154(b) by 28 days.

(21) Appl. No.: 13/581,111

(22) PCT Filed: Feb. 24, 2011

(86) PCT No.: PCT/ES2011/070118
§ 371 (c)(1),
(2), (4) Date: Nov. 7, 2012

(87) PCT Pub. No.: WO2011/104410
PCT Pub. Date: Sep. 1, 2011

(65) Prior Publication Data
US 2013/0209530 A1    Aug. 15, 2013

(30) Foreign Application Priority Data
Feb. 26, 2010 (ES) .................. P201030286

(51) Int. Cl.
| | |
|---|---|
| *A61K 8/11* | (2006.01) |
| *A61K 8/64* | (2006.01) |
| *A61Q 19/00* | (2006.01) |
| *A61K 8/49* | (2006.01) |
| *A61K 8/67* | (2006.01) |
| *A23L 33/10* | (2016.01) |
| *A23L 33/175* | (2016.01) |
| *A23L 33/16* | (2016.01) |
| *A23P 10/30* | (2016.01) |
| *A23L 33/15* | (2016.01) |
| *A61K 9/14* | (2006.01) |

(52) U.S. Cl.
CPC ............... *A61K 8/11* (2013.01); *A23L 33/10* (2016.08); *A23L 33/15* (2016.08); *A23L 33/16* (2016.08); *A23L 33/175* (2016.08); *A23P 10/30* (2016.08); *A61K 8/498* (2013.01); *A61K 8/64* (2013.01); *A61K 8/67* (2013.01); *A61K 9/14* (2013.01); *A61Q 19/00* (2013.01); *A61K 2800/412* (2013.01)

(58) Field of Classification Search
CPC ...................................................... A61K 8/11
See application file for complete search history.

(56) References Cited

U.S. PATENT DOCUMENTS

| | | | | |
|---|---|---|---|---|
| 4,146,649 A | * | 3/1979 | Siegel et al. ........... | 514/777 |
| 5,945,409 A | * | 8/1999 | Crandall ............... | A61K 8/365 514/159 |
| 6,337,131 B1 | * | 1/2002 | Rupaner ............... | B05D 5/061 428/212 |
| 2004/0228894 A1 | * | 11/2004 | Nojiri ................... | A61K 8/342 424/401 |
| 2010/0233219 A1 | * | 9/2010 | Aimi ..................... | A61K 49/1833 424/401 |

FOREIGN PATENT DOCUMENTS

| | | |
|---|---|---|
| EP | 2011472 A1 | 3/2007 |
| EP | 1844758 A1 | 10/2007 |
| JP | 2009040722 | 2/2009 |
| WO | 2007122613 A1 | 11/2007 |
| WO | 2009101612 A2 | 8/2009 |

OTHER PUBLICATIONS

Rawlings et al., JID, 124:099-1110, 2005.*
Horii et al., Brit J Dermatol, 121, 587-592, 1989.*
Pan, Xiaoyun, et al.; "Micellization of Casein-graft-Dextran Copolymer Prepared through Maillard Reaction," Biopolymers, 2006, pp. 29-38, vol. 81.
International Search Report, dated Apr. 8, 2011.
Japanese Office Action, dated Sep. 2, 2014 (do not have JP Office Action).
Varothai, Supenya, et al.; "Moisturizers for patients with atopic dermatitis," Asian Pac J Allergy Immunol, 2013, pp. 91-98, vol. 31.
Verdier-Sévrain, Sylvie, et al.; "Skin hydration: a review on its molecular mechanisms," Journal of Cosmetic Dermatology, 2006, pp. 75-82, vol. 6.
Lynde, C.W., MD, FRCPC; Moisturizers: What They Are And How They Work, http://www.skintherapyletter.com/dry-skin/how-moisturizers-work/, 2001, vol. 6.

* cited by examiner

*Primary Examiner* — Kyle A Purdy
(74) *Attorney, Agent, or Firm* — Tristan A. Fuierer; Olive Law Group, PLLC

(57) ABSTRACT

The present invention relates to nanoparticles for encapsulating compounds, the preparation and uses thereof, comprising a casein matrix, a basic amino acid and a metal selected from a divalent metal, a trivalent metal and combinations thereof. Said nanoparticles can encapsulate a water soluble or fat soluble biologically active compound. The invention is applicable in the food, pharmaceutical and cosmetic sectors and in the nanotechnology sector.

14 Claims, 8 Drawing Sheets

A

B

NANOPARTICLES FOR THE ENCAPSULATION OF COMPOUNDS, PREPARATION THEREOF AND USE OF SAME

CROSS-REFERENCE TO RELATED APPLICATIONS

This application is filed under the provisions of 35 U.S.C. § 371 and claims the priority of International Patent Application No. PCT/ES2011/070118 filed on 24 Feb. 2011 entitled "Nanoparticles for the Encapsulation of Compounds, Preparation Thereof and Use of Same" in the name of Maite AGUEROS BAZO, which claims priority of ES 201030286 filed on 26 Feb. 2010, both of which are hereby incorporated by reference herein in their entirety.

FIELD OF THE INVENTION

The present invention is encompassed in the food, pharmaceutical and cosmetic sectors and in the nanotechnology sector and consists of the encapsulation of biologically active compounds using casein as a coating agent.

BACKGROUND OF THE INVENTION

The food industry needs to evolve technologically to meet new consumer demands. Nanotechnology presents a great potential to revolutionize the food industry as through this technology it is possible to encapsulate biologically active compounds [BAC], e.g., flavors, vitamins, minerals, essential oils, antioxidants, prebiotics, etc., in order to obtain numerous benefits, for example, to increase the shelf life of the product; to reduce the amount of BAC to be used; to control the release thereof; to increase the bioavailability thereof; to mask unwanted flavors, etc.

When designing a carrier suitable for encapsulating a BAC, it is very important to correctly select the material used as the coating agent or matrix; to that end, the dosage form, the toxicity thereof, the product (food, cosmetic, pharmaceutical, etc.) in which the formulation will be incorporated, etc., among other factors, must be taken into account. In the field of food nanotechnology, it is not recommendable to use synthetic polymers as they may present toxicity problems. Natural polymers do not have these drawbacks; however, their use implies the development of more complicated particle production methods; furthermore, in most cases, the particle size obtained (greater than 100 μm in many cases) is difficult to control, therefore such nanoparticles may be noticed by the consumer and change the organoleptic characteristics of the target food.

Proteins are among the materials traditionally used as BAC coating agents. The use of casein as a carrier for encapsulating hydrophobic BAC for its application in foods has been described (CA2649788 and EP2011472).

Folic acid (pteroylmonoglutamic acid or vitamin B9), a type-B water soluble vitamin included within the folate group, is essential for important biochemical processes such as DNA synthesis. The lack thereof is associated with the presence of megaloblastic anemia, Alzheimer's disease, Down syndrome, humor disorders, some types of cancer (colon cancer, cervical cancer, leukemia, pancreatic cancer), neural tube defects during fetal development, complications during pregnancy and male infertility. However, it can not be synthesized by the organism; therefore it must be supplied through various supplements or diet.

Although folates are present naturally in foods (e.g., fruits and vegetables), fundamentally in the form of polyglutamates, their bioavailability, typically 50% or less, is incomplete. Therefore, the consumption of foods fortified with folic acid may form a complementary option to increase the intake of said vitamin in those cases in which the intake of folates is lower than that recommended. Nevertheless, the bioavailability of folic acid added to foods is not complete due to, among other causes, the matrix effect (folic acid may be linked to a food component thus preventing its absorption), or the presence of any component in the food which reduces its bioavailability. Furthermore, folic acid is not well absorbed when it is not solubilized in the intestine. Supplements or fortifications with folic acid administered by means of capsules, tablets, etc., have the drawback of, upon breaking down in the stomach due to gastric acids, folic acid precipitating, being converted into its less soluble form, whereby only part of the supplied folic acid reaches the intestine.

In addition, the fortification of foods with folates or with folic acid is a complicated process as both folates and their derivatives as well as folic acid are sensitive to, among other factors, temperature, light, and pH changes; therefore their stability is compromised by food processing conditions and the bioactive amount of the vitamin available to the consumer may be greatly reduced. Thus, when fortifying foods with said vitamin, it is necessary to take these aspects into account as the greatest losses may take place during the storage and preparation of foods.

The enrichment of foods with folic acid, fundamentally in dairy and cereal products, has been described. Dietary supplements (EP2002839) or foods enriched with folic acid or folates, such as sausage meats (ES2302571), dairy products (EP1941804), infant foods (US4753926), or even chicken, pork or beef based canned foods (RU2223672 and RU2213493) have also been described. However, in the described cases neither the possible interactions of the vitamin with the food matrix nor the bioavailability thereof are contemplated.

A method for obtaining alginate and pectin microcapsules containing folic acid to protect it from the environmental factors that lead to its degradation, such as gastric conditions, achieving its release into intestine, has also been described. However, the microcapsules obtained are excessively large, which affects the organoleptic characteristics of the target food. A method for encapsulating folic acid in poly(lactic-co-glycolic acid) (PLGA) nanospheres and achieving a sustained release thereof has also been designed; although the results were positive, its application in foods is compromised by the use of that polymer as it is restricted to the areas of medicine and pharmacy.

Therefore, there is a need to develop BAC encapsulation systems, preferably water soluble, more preferably acidic water soluble BAC, e.g., folic acid, which entirely or partly overcome the aforementioned drawbacks.

SUMMARY OF THE INVENTION

It has now surprisingly been found that nanoparticles formed with casein further comprising a basic amino acid (e.g., arginine or lysine) and a metal suitable for food (e.g., calcium), form a new encapsulation and stabilizing system for biologically active compounds (BAC) that are both water and fat soluble, preferably water soluble, more preferably acidic water soluble BAC, for the application thereof in foods, cosmetics and pharmacy.

Therefore, in one aspect, the invention relates to nanoparticles comprising a casein matrix, a basic amino acid and a food-grade metal selected from a divalent metal, a trivalent metal and combinations thereof. Said nanoparticles can be used as technological additives; they further have the capacity for encapsulating a BAC, preferably a water soluble BAC, more preferably acidic water soluble BAC, such as for example a type B or C vitamin, such as folic acid, pantothenic acid and ascorbic acid, or other hydrophilic compounds, although they can also incorporate fat soluble BAC.

Said nanoparticles are stable and capable of protecting the BAC from degradation by external agents, e.g., light, pH changes, oxidation, etc., both during product processing (e.g., food, pharmaceutical or cosmetic product) and during storage, and, furthermore, when they are applied in food, they protect the BAC from the acidic conditions of the stomach, preventing its release along the gastric tract, thus avoiding its precipitation and, therefore, avoiding reduced bioavailability. Furthermore, it has been found that said nanoparticles are capable of dissolving in (simulated) intestinal medium facilitating the complete release of the BAC in the intestine for its correct absorption, and further avoiding toxicity problems of any type. Advantageously, said nanoparticles are inert in the food in which they are introduced, thus avoiding the BAC from reacting with different components of the matrix and reducing its bioavailability.

Additionally, one of the most important features of the nanoparticles provided by this invention lies in using casein as a natural carrier for protecting the BAC from both the environmental conditions and the gastric conditions, facilitating its release in the intestine and thus improving its bioavailability, as casein per se has demonstrated nutritional properties such that it complements the beneficial effects of the BAC itself.

In another aspect, the invention relates to a process for producing said nanoparticles. Said process is simple and applicable at an industrial scale. Advantageously, said process does not include synthetic or reactive polymers which are not approved as food additives, minimizing the inclusion of surfactants or emulsifiers, and it allows obtaining nanoparticles on a nanometric scale, with a controllable particle size.

In a particular embodiment, said process further comprises drying the suspension containing said nanoparticles in order to obtain the formulation in powder form, maintaining the BAC stable over time; this type of powder formulation is particularly suitable for its use in solid foods. Advantageously, said drying treatment is carried out in the presence of a nanoparticle protective agent. The nanoparticles containing a BAC thus obtained can be easily suspended in aqueous medium, protecting the BAC from degradation in solution. The end product obtained is stable and protects the BAC throughout long storage periods and is further applicable to different types of foods, both liquids (e.g., drinks, etc.) and solids.

In another aspect, the invention relates to a composition comprising said nanoparticles for their use in the food, pharmaceutical or cosmetic sectors. In fact, said nanoparticles can be incorporated in creams, gels and hydrogels in order to obtain stable cosmetic preparations suitable for use in this field. Said nanoparticles can also be formulated with excipients suitable for the administration of said nanoparticles by topical route.

In another aspect, the invention relates to a foodstuff, comprising said composition based on the casein nanoparticles provided by this invention. In a particular embodiment, said foodstuff is in liquid, semi-solid or solid form.

DETAILED DESCRIPTION OF THE INVENTION

Figure 1:
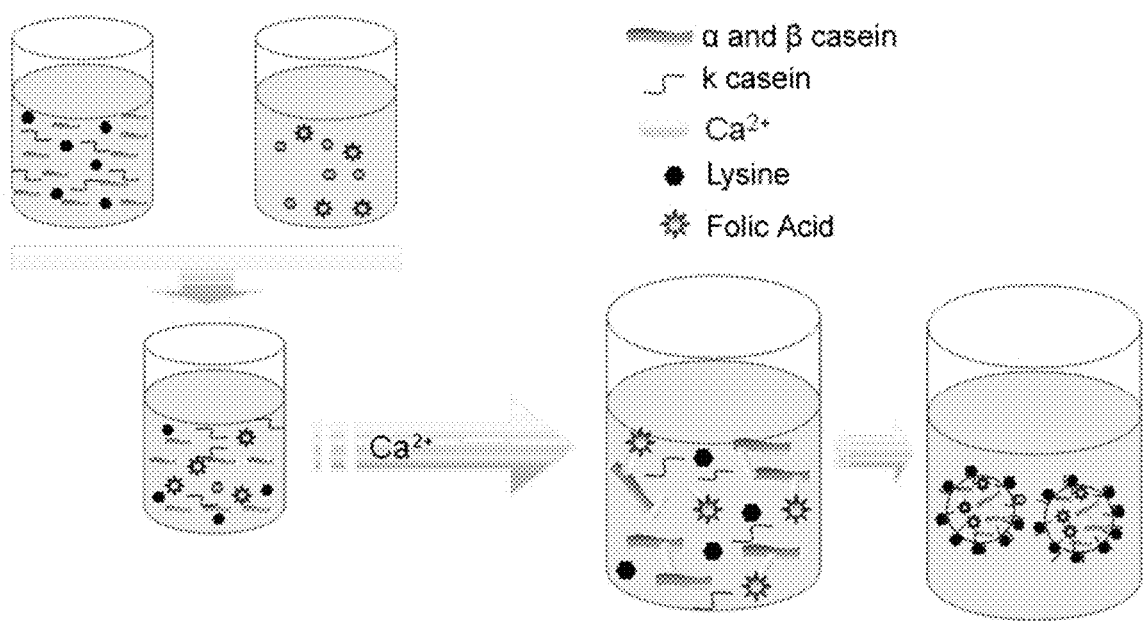
FIG. 1 shows a schematic depiction of a particular embodiment of the process of the invention applied for obtaining the casein nanoparticles containing folic acid.

The present invention provides casein nanoparticles and methods for encapsulating biologically active compounds (BAC) in order to preserve them from degradation by external agents, such as light, pH change, oxidation, etc.

Definitions

For the purpose of facilitating the comprehension of the present invention, the meaning of some terms and expressions as used in the context of the invention are set forth below.

As it is used herein, a "basic amino acid" includes lysine, arginine and histidine.

As it is used herein, "casein" refers to a conjugated protein forming approximately 80% of the total milk proteins. It is a phosphoprotein type protein which is within the definition of globulins; it is soluble; has a high water retention capacity and precipitates at an approximate pH of 4.6 at 20° C. It is formed by four fundamental fractions ($\alpha$s1-casein, $\alpha$s2-casein, $\beta$-casein and $\kappa$-casein) differentiated from one another by their amino acids composition, their charge distribution and their tendency to form aggregates in the presence of calcium. In milk, caseins form large colloidal particles between 50 to 600 nm in diameter (approximately 150 nm on average) referred to as "casein micelles". These particles are formed by hydrophobic interactions and by calcium phosphate complexing by phosphoserine radicals present in the casein structure. Said micelles form a very stable colloidal system in milk, being one of the main causes for its color, heat stability and coagulation by rennin.

As it is used herein, a "biologically active compound" or "BAC" refers to any fat and water soluble compound having nutritional, therapeutic and/or cosmetic activity. Non-limiting illustrative examples of BAC according to the present invention include amino acids, antimicrobial agents, aromatizing agents, preservatives, sweeteners, steroids, drugs, hormones, lipids, peptides, polynucleotides, polysaccharides, proteins, proteoglycans, flavoring agents, vitamins, etc.

As it is used herein, a "water soluble biologically active compound" or "water soluble BAC" refers to a compound having nutritional, therapeutic and/or cosmetic activity and which is soluble (very soluble, freely soluble, soluble, sparingly soluble or slightly soluble) in an aqueous solution according to the criteria defined by the Royal Spanish Pharmacopoeia:

| Descriptive Terms | Approximate volumes of solvent in milliliters (mL) per gram of solute, referring to a temperature comprised between 15° C. and 25° C. |
|---|---|
| Very soluble | Less than 1 |
| Freely soluble | from 1 to 10 |
| Soluble | from 10 to 30 |
| Sparingly soluble | from 30 to 100 |
| Slightly soluble | from 100 to 1,000 |
| Very slightly soluble | from 1,000 to 10,000 |
| Practically insoluble | greater than 10,000 |

Non-limiting illustrative examples of water soluble BACs include vitamins, for example, vitamins from the B or C families and the derivatives, salts or esters thereof; hyaluronic acid, chondroitin sulphate, thioctic acid, the salts or esters thereof, etc. In a particular embodiment, said water soluble BAC is selected from the group consisting of folic acid, 4-aminobenzoic acid, niacin, pantothenic acid, thiamine monophosphate, thiamine pyrophosphate, thiamine triphosphate, ascorbic acid, pteroylpolyglutamic acids (folic acid derivatives: folate polyglutamates; polyglutamate folates), folinic acid, nicotinic acid, hyaluronic acid, thioctic acid (alpha lipoic acid), p-coumaric acid, caffeic acid, the pharmaceutically or cosmetically acceptable or food-grade derivatives, esters or salts thereof, and mixtures thereof.

As it is used herein, a "fat soluble biologically active compound" or "fat soluble BAC" refers to a compound having nutritional, therapeutic and/or cosmetic activity and which is soluble (very soluble, freely soluble, soluble, sparingly soluble or slightly soluble) in fats and oils according to the criteria defined by the Royal Spanish Pharmacopoeia. Non-limiting illustrative examples of fat soluble BAC include vitamins, for example, vitamins from the A, D, E, K families and derivatives thereof, phospholipids, carotenoids (carotenes, lycopene, lutein, capsanthin, zeaxanthin etc.), omega-3 fatty acids (docosahexaenoic acid (DHA), eicosapentaenoic acid (EPA), etc.), phytostanols and phytosterols (sitosterol, campesterol, stigmasterol, etc.), polyphenols (quercetin, rutin, resveratrol, kaempferol, myricetin, isorhamnetin, etc.) and derivatives thereof.

A product is said to be "food-grade" when its use in human or animal food is safe according to the Codex Alimentarius of a country or of an organization, for example, the Food and Agriculture Organization (FAO) of the United Nations or the World Health Organization (WHO); consequently, a "food-grade" product is a non-toxic product "suitable for use thereof in food" and therefore both expressions are synonyms and are indistinctly used in this description.

As it is used herein, a "divalent metal" includes any metal element the valence of which is 2, for example, an alkaline-earth metal, e.g., calcium, magnesium, zinc, etc., or, if it has several valences, one of them is 2, for example, iron, etc., on the proviso that it is pharmaceutically or cosmetically acceptable, or suitable for use in food.

As it is used herein, a "trivalent metal" includes any metal element the valence of which is 3, or, if it has several valences, one of them is 3, for example, iron, etc., on the proviso that it is pharmaceutically or cosmetically acceptable, or suitable for use in food.

As it is used herein, "nanoparticle" refers to spherical type or similar shaped colloidal systems with a size less than 1 micrometer ($\mu$m), preferably in the order of 10 to 900 nanometers (nm).

As it is used herein, "mean size" refers to the average diameter of the nanoparticle population that moves together in an aqueous medium. The mean size of these systems can be measured by standard processes known by the person skilled in the art, and which are described, for example, in the experimental part (see below). The nanoparticles of the invention are characterized by having a mean particle size less than 1 $\mu$m, typically comprised between 1 and 999 nm, preferably between 10 and 900 nm, more preferably between 50 and 500 nm, still more preferably between 100 and 200 nm. In a particular embodiment, the nanoparticles of the invention have a mean particle size comprised between 50 and 200 nm, preferably about 140 nm approximately.

Nanoparticles

In one aspect, the invention relates to a nanoparticle, hereinafter the nanoparticle of the invention, comprising a casein matrix, a basic amino acid and a metal selected from a divalent metal, a trivalent metal and combinations thereof.

In a particular embodiment, said basic amino acid is selected from the group consisting of arginine, lysine, histidine and mixtures thereof.

In another particular embodiment, said metal is preferably a food-grade divalent metal selected from the group consisting of calcium, magnesium, zinc, iron (in their divalent form) and combinations thereof.

In another particular embodiment, said metal is a food-grade trivalent metal, such as, for example, iron in its trivalent form.

The nanoparticles of the invention can be used as technological additives, for example, as fat substitutes, etc. The nanoparticles of the invention further have the capacity for encapsulating a biologically active compound (BAC).

Thus, in another particular embodiment, the nanoparticle of the invention further comprises a biologically active compound (BAC). Said BAC can be a water soluble BAC or a fat soluble BAC; in this case the nanoparticle of the invention is occasionally identified in this description as "loaded nanoparticle of the invention".

In a particular embodiment said BAC is a water soluble BAC, preferably acidic water soluble BAC. In a more particular embodiment, said water soluble BAC is selected from the group consisting of:
a) a vitamin from the B or C family;
b) a vitamin derivative according to a);
c) a compound selected from hyaluronic acid, chondroitin sulphate and thioctic acid;
d) a salt or an ester of any of the aforementioned compounds a)-c); and
e) combinations thereof.

In a specific embodiment, said water soluble BAC is selected from the group consisting of folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids (folic acid derivatives: folate polyglutamates; polyglutamate folates), folinic acid, nicotinic acid, hyaluronic acid, thioctic acid or alpha lipoic acid, p-coumaric acid, caffeic acid, the pharmaceutically or cosmetically acceptable or food-grade derivatives, esters or salts thereof, and mixtures thereof.

In a specific embodiment, said BAC is acidic water soluble BAC such as folic acid, pantothenic acid, ascorbic acid, etc.

Without wishing to be bound by any theory, it is believed that in the presence of metal such as divalent metal (e.g., calcium), α and β caseins aggregate due to their hydrophilic and surface charge being lost when the phosphoserine radicals present in the structure thereof bind to the cation part. The water soluble BAC, preferably acidic (e.g., folic acid), also interacts electrostatically with said metal, therefore it would be trapped in the hydrophobic matrix generated by these types of casein. The κ casein in turn does not react with the metal (e.g., calcium), therefore it is bound by its hydrophobic part to the particle, its water soluble fraction being in contact with the external aqueous medium. Said water soluble fraction has, in addition to a high proportion of carbonyl groups (acid groups of amino acids such as glutamic or aspartic acid), polar groups corresponding to the seryl and threonyl residues bound to tri- and tetra-saccharides. It is thus considered that after the formation of the nanoparticles, the basic amino acid (e.g., lysine) present in the solution would be adhered to the surface of these nanoparticles due to its electrostatic interaction [e.g., they can be covalent bonds after undergoing heating during their passage through the spray dryer (where appropriate)] with the carboxylic groups of said fraction. FIG. 1 shows a schematic depiction of the loaded nanoparticles of the present invention comprising a casein matrix, lysine (basic amino acid) and calcium (divalent metal).

In another specific embodiment said BAC is a fat soluble BAC although in this case it would be necessary to form a preferably homogenous suspension of BAC in aqueous medium, or more preferably to dissolve the BAC in an organic solution, slowly adding said aqueous suspension or said organic solution into the solution containing the source of casein (e.g., caseinate) and incubate the mixture.

The trapping mechanism would be different from that described for water soluble BAC because fat soluble BAC would be trapped in the inner hydrophobic fraction of the nanoparticles due to the affinity between both fractions, regardless of whether or not they have the capacity to interact with the (divalent or trivalent) metal.

In a particular embodiment, said BAC is a fat soluble BAC selected from vitamins, for example, vitamins from the A, D, E, K families and derivatives thereof, phospholipids, carotenoids (carotenes, lycopene, lutein, capsanthin, zeaxanthin, etc.), omega-3 fatty acids (e.g. DHA, EPA, etc.), amino acids (e.g., iso-leucine, leucine, methionine, phenylalanine, tryptophan, and valine), phytostanols and phytosterols (e.g. sitosterol, campesterol, stigmasterol, etc.), polyphenols (e.g. quercetin, rutin, resveratrol, kaempferol, myricetin, isorhamnetin, etc.) and derivatives thereof.

The BAC:casein ratio by weight in the loaded nanoparticle of the invention may vary within a broad range; in a non-limiting illustrative manner, the BAC:casein ratio by weight in the loaded nanoparticle of the invention may be comprised between 1:1 and 1:200, preferably between 1:10 and 1:80, more preferably between approximately 1:15 and 1:35. In a particular embodiment, the BAC is a water soluble BAC, and the (water soluble) BAC:casein ratio by weight in the loaded nanoparticle of the invention is comprised between 1:1 and 1:50, preferably between 1:10 and 1:30, more preferably between approximately 1:15 and 1:20. In another particular embodiment, the BAC is a fat soluble BAC, and the (fat soluble) BAC:casein ratio by weight in the loaded nanoparticle of the invention is comprised between 1:1 and 1:200, preferably between 1:10 and 1:80, more preferably between approximately 1:20 and 1:35.

Additionally, if desired, the nanoparticles of the invention, both those that are loaded with a BAC and those that are not, may incorporate an antioxidant, e.g., ascorbic acid (vitamin C), etc., in their formulation for the purpose of increasing their stability with regard to temperature and oxidation. In a particular embodiment, the BAC is folic acid and the antioxidant is ascorbic acid which seems to act by protecting the folic acid from degradation by ultraviolet radiation, pH change, heat, oxygen, etc., and further provides the nutritional support of the ascorbic acid. Said antioxidant could be co-encapsulated with the BAC or introduced in the coating of the nanoparticles of the invention.

Process for Obtaining Nanoparticles

In another aspect, the invention relates to a process for producing nanoparticles comprising a casein matrix, a basic amino acid and a metal selected from a divalent metal, a trivalent metal and combinations thereof (nanoparticles of the invention), hereinafter "process [1] of the invention", which comprises:
a) preparing an aqueous solution containing a source of casein and a basic amino acid; and
b) adding an aqueous solution of a metal selected from a divalent metal, a trivalent metal and combinations thereof to the solution of step a).

In another aspect, the invention also relates to a process for producing nanoparticles comprising a casein matrix, a basic amino acid, a metal selected from a divalent metal, a trivalent metal and combinations thereof, and a biologically active compound (loaded nanoparticles of the invention), hereinafter "process [2] of the invention", which comprises:
a) mixing (i) an aqueous solution containing a source of casein and a first basic amino acid with (ii) a solution containing a biologically active compound; and
b) adding an aqueous solution of a metal selected from a divalent metal, a trivalent metal and combinations thereof to the mixture resulting from step a).

In step a) of the process [1] of the invention, an aqueous solution containing a source of casein and a basic amino acid is prepared by conventional methods known by persons skilled in the art, for example, by means of adding said source of casein and the basic amino acid to an aqueous medium.

In step a) of the process [2] of the invention, an aqueous solution (i) containing a source of casein and a basic amino acid is mixed with a solution (ii) containing a BAC. The nature and composition of said solution (ii) containing the BAC may vary depending on the type and nature of the BAC. Thus, in a particular embodiment, when the BAC is a water soluble BAC, said solution (ii) containing the BAC is an aqueous solution; in another particular embodiment, when the BAC is acidic water soluble BAC, said solution (ii) containing the BAC is an aqueous solution further comprising a second basic amino acid; and, in another particular embodiment, when the BAC is a fat soluble BAC, said solution (ii) containing the BAC is a suspension thereof in an aqueous medium or preferably an organic solution, more preferably an organic solution of a water miscible solvent such as an alcohol, for example, ethanol.

The casein which can be used to put both processes [processes [1] and [2] of the invention] into practice can come from virtually any source of casein, for example, milk, beans, etc. The casein may be found in said solution in the form of acid casein or caseinate. In a particular embodiment, said source of casein comprises casein in the form of caseinate, preferably sodium caseinate. Although calcium caseinate and phosphocalcium could also be used, they are less advantageous in practice because calcium is used to form the nanoparticles after mixing the caseinate with the active ingredient, therefore, if the caseinate solution already has calcium in the medium, putting said processes into practice can be seriously compromised.

The amount of casein that can be contained in the aqueous solution formed in step a) of the process [1] of the invention, as well as the aqueous solution (i) [containing a source of casein and a first basic amino acid] used in step a) of the process [2] of the invention may vary within a broad range; however, in a particular embodiment, the amount of casein contained in said aqueous solution is comprised between 0.1% and 10% (w/v), preferably between 0.5% and 5%, more preferably between 1% and 3%.

The basic amino acid contributes to dissolving the casein and, where appropriate, the BAC, particularly acid water soluble BACs, therefore it plays a very important role in the production of the BAC that are loaded with the nanoparticles of the invention and those that are not. In fact, it seems that upon increasing the pH of the solution, the basic amino acid allows dissolving the caseinate without the need of using inorganic salts, and it further acts as a base for maintaining the hydrophilic ends of the kappa (κ) fractions of the casein in an anionic form, such that the particles with negative surface charge are maintained in suspension and do not aggregate due to electrostatic repulsions.

The basic amino acid which can be used for putting both processes [processes [1] and [2] of the invention] into practice is selected from the group consisting of arginine, lysine, histidine and mixtures thereof, preferably, from arginine, lysine and mixtures thereof. The basic amino acid, which can be inside or outside the nanoparticles of the invention, plays a fundamentally technological role as it facilitates the dissolution of the components prior to the formation of the nanoparticles and it maintains suitable pH after obtaining them on both sides of the nanoparticle (inside and outside). By means of illustration, folic acid is slightly soluble in water but freely soluble in slightly alkaline aqueous solution, therefore the presence of the basic amino acid aids in dissolving folic acid.

In a particular embodiment of the process [2] of the invention, when the BAC is acid water soluble BAC said solution (ii) containing the BAC is an aqueous solution further comprising a second basic amino acid (in order to prevent the BAC from precipitating). Although the possibility of using two different basic amino acids is contemplated in that case, in a particular embodiment the basic amino acid used in preparing the aqueous solution containing a source of casein (first basic amino acid) and that used in preparing the aqueous solution containing a BAC (second basic amino acid) is the same and is selected from the group consisting of arginine, lysine, histidine and mixtures thereof, preferably from arginine, lysine and mixtures thereof.

The amount of basic amino acid that can be contained in the solution formed in step a) of the process [1] of the invention and in solution (i) of step a) of the process [2] of the invention may vary within a broad range and generally depends on the basic amino acid used. Therefore, although the basic amino acid:casein ratio by weight may greatly vary, in a particular embodiment the basic amino acid:casein ratio by weight in the solution formed in step a) of the process [1] of the invention or in solution (i) of the process [2] of the invention is comprised between 1:1 and 1:50, preferably between 1:10 and 1:40, more preferably approximately 1:12 when the basic amino acid used is lysine or approximately 1:25 when the basic amino acid used is arginine.

When the BAC is acidic water soluble BAC, the solution (ii) of step a) of the process [2] of the invention containing said BAC further comprises a second basic amino acid, which, as has been previously mentioned, may be to the same as or different from said first basic amino acid; in this case, the basic amino acid:casein ratio in the process [2] of the invention, i.e., after mixing solutions (i) and (ii) of step a) of said process, is comprised between 1:1 and 1:50, preferably between 1:5 and 1:20, more preferably approximately 1:6 when the basic amino acid used is lysine or approximately 1:9 when the basic amino acid used is arginine.

Both process [1] of the invention and process [2] of the invention comprise the step of adding a) an aqueous solution of a metal selected from a divalent metal, a trivalent metal and combinations thereof [step b)] to the solution of the step. Without wishing to be bound by any theory, it is believed that said metal, such as a divalent metal (e.g., calcium), allows creating a bridge inside the loaded nanoparticle of the invention which aids in stabilizing the BAC, particularly when the BAC is a water soluble BAC, preferably acidic water soluble BAC, or a water soluble BAC capable of interacting with said metal (e.g., calcium), for example, folic acid, pantothenic acid or a vitamin of the B or C group or derivatives thereof; in this case, it seems that said metal, for example, said divalent metal (e.g., calcium), acts by as a bridge between the casein (in the form of caseinate) and the BAC, preferably a water soluble BAC, more preferably acidic water soluble BAC, or a water soluble BAC capable of interacting with said metal, leaving said BAC trapped in the hydrophobic fraction of the loaded nanoparticles of the invention.

In a particular embodiment said metal is a divalent metal selected from calcium, magnesium, zinc, iron in divalent form and combinations thereof, preferably calcium. In another particular embodiment said metal is a trivalent metal such as iron in trivalent form.

Although virtually any aqueous solution of calcium, advantageously food-grade solution, [see the "Codex General Standard for Food Additives" GSFA Online for a calcium salt ratio used in food-microencapsulation] can be used for putting said processes [1] and [2] of the invention into practice, in a particular embodiment, said aqueous solution of a calcium salt is selected from the group consisting of calcium chloride, calcium acetate, calcium gluconate, calcium lactate, calcium sorbate, calcium ascorbate, calcium citrate, calcium propionate, calcium sulphate and mixtures thereof, preferably calcium chloride. In practice, calcium carbonate or calcium alginate are not recommendable because they are salts that are insoluble or very slightly soluble in water. Similarly, any aqueous solution of food-grade magnesium, zinc or iron in divalent or trivalent form can be used for putting said processes [1] and [2] of the invention into practice.

The metal:casein ratio by weight, wherein "metal" refers to said metal selected from a divalent metal, a trivalent metal and combinations thereof, may vary within a broad range; however, in a particular embodiment, the metal:casein ratio by weight is comprised between 1:5 and 1:15, preferably between 1:7 and 1:10, more preferably about 1:8.5. In a particular embodiment, said metal is a divalent metal.

The process [2] of the invention leads to obtaining loaded nanoparticles of the invention and, to that end, step a) comprises mixing (i) an aqueous solution containing a source of casein and a first basic amino acid with (ii) a solution containing a BAC. The characteristics of said BAC have been previously mentioned. In a particular embodiment said BAC is a water soluble BAC, preferably acidic water soluble BAC, for example, folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids (folic acid derivatives: folate polyglutamates; polyglutamate folates), folinic acid, nicotinic acid, hyaluronic acid, thioctic acid, p-coumaric acid, caffeic acid, the pharmaceutically or cosmetically acceptable or food-grade derivatives, esters or salts thereof, and mixtures thereof. In another particular embodiment, said BAC is a fat soluble BAC, for example, a vitamin of the A, D, E, K families and derivatives thereof, a phospholipid, a carotenoid (e.g., carotenes, lycopene, lutein, capsanthin, zeaxanthin, etc.), an omega-3 fatty acid (e.g., DHA, EPA, etc.), an amino acid (e.g., iso-leucine, leucine, methionine, phenylalanine, tryptophan, and valine), a phytostanol or a phytosterol (e.g., sitosterol, campesterol, stigmasterol, etc.), a polyphenol (quercetin, rutin, resveratrol, kaempferol, myricetin, isorhamnetin, etc.) or derivatives thereof.

The BAC:casein ratio by weight in the loaded nanoparticle of the invention may vary within a broad range; in a non-limiting illustrative manner, the BAC:casein ratio by weight in the loaded nanoparticle of the invention may be comprised between 1:1 and 1:200, preferably between 1:10 and 1:80, more preferably between approximately 1:15 and 1:35. In a particular embodiment, the BAC is a water soluble BAC, and the (water soluble) BAC:casein ratio by weight in the loaded nanoparticle of the invention is comprised between 1:1 and 1:50, preferably between 1:10 and 1:30, more preferably between approximately 1:15 and 1:20. In another particular embodiment, the BAC is a fat soluble BAC, and the ratio between (fat soluble) BAC:casein by weight in the loaded nanoparticle of the invention is comprised between 1:1 and 1:200, preferably between 1:10 and 1:80, more preferably between approximately 1:20 and 1:35.

Likewise, the basic amino acid:BAC ratio by weight (corresponding to the aqueous solution (ii) containing acidic water soluble BAC and a second basic amino acid used in step a) of the process [2] of the invention) may vary within a broad range; however, in a particular embodiment, the basic amino acid: (acid water soluble) BAC ratio by weight in said solution (ii) is comprised between 1:0.1 and 1:3, preferably between 1:0.5 and 1:1, more preferably about 1:0.75.

As has been previously mentioned, the nanoparticles of the invention, both those that are loaded with a BAC and those that are not, may incorporate an antioxidant, e.g., ascorbic acid (vitamin C), etc., in their formulation for the purpose of increasing their stability with regard to temperature and oxidation. In this case, said antioxidant could be co-encapsulated with the BAC (where appropriate) or in the coating of the nanoparticles of the invention; to that end, said processes [1] and [2] of the invention will be suitably adapted to incorporate the antioxidant in the formulation of the nanoparticles, for example, by adding the antioxidant to the aqueous solution containing said BAC and a basic amino acid.

In a particular embodiment, the BAC is folic acid and the antioxidant is ascorbic acid which seems to act by protecting the folic acid from degradation by ultraviolet radiation, pH change, heat, oxygen, etc., and further provides the nutritional support of the ascorbic acid. Said antioxidant could be co-encapsulated with the BAC or introduced in the coating of the nanoparticles of the invention.

Additionally, if desired, both process [1] of the invention and process [2] of the invention may include one or more additional steps for stabilizing obtained nanoparticles by means of using different treatments.

In a particular embodiment, said stabilizing treatment comprises subjecting the suspension containing the nanoparticles of the invention formed, both those that are loaded with a BAC and those that are not, to a high pressure treatment, for example, at a pressure comprised between 100 and 800 MPa, typically between 350 and 600 MPa. In a particular embodiment, said treatment comprises subjecting the suspension of nanoparticles to cycles of 3 to 5 minutes at a pressure of 100 MPa to 800 MPa, typically between 350 and 600 MPa; in fact, a pressure of 400 MPa provides good results.

In another particular embodiment, said stabilizing treatment comprises subjecting the suspension containing the nanoparticles of the invention formed, both those that are loaded with a BAC and those that are not, to a UHT (Ultra High Temperature) treatment, for example, to a temperature comprised between 130° C. and 140° C. for 2 to 5 seconds, followed by rapid cooling.

Likewise, if desired, both process [1] of the invention and process [2] of the invention may include a drying step for drying the suspension containing the nanoparticles formed in order to obtain the nanoparticles of the invention, both those that are loaded with a BAC and those that are not, in the form of a powder. This form of presentation of said nanoparticles contributes to their stability and is further particularly useful for their eventual application in solid foods, such as flour, bread, pastry products, cereals, milk powder, etc., as well as in cosmetic and/or pharmaceutical products.

Virtually any conventional technique or method suitable for drying suspensions containing nanoparticles can be used to perform this drying step; however, in a particular embodiment, the drying of the suspension containing nanoparticles is carried out by means of spray drying or by means of lyophilization. This treatment is generally carried out by adding a suitable protective agent of said nanoparticles, such as a saccharide, for example, lactose, trehalose, mannitol, sucrose, maltodextrine, glucose, sorbitol, maltose, etc., and mixtures thereof to the suspension of the nanoparticles. Said protective agent protects the nanoparticles of the invention against heat degradation as well as oxidation during the drying process.

The casein:saccharide ratio by weight may vary within a broad range; however, in a particular embodiment, the casein:saccharide ratio by weight is comprised between 1:1 and 1:4, preferably about 1:2.

Likewise, in a particular embodiment, the solution containing the saccharide could further contain an antioxidant agent, such as ascorbic acid (vitamin C), etc.; in this case, the casein:saccharide:antioxidant agent, for example, vitamin C, ratio by weight could be 1:0.75-2.5:0.01-1.5, preferably 1:2.0:0.10.

The nanoparticles of the invention obtained according to process [1] of the invention, i.e., the nanoparticles comprising a casein matrix, a basic amino acid and a metal selected from a divalent metal, a trivalent metal and combinations thereof, produced by means of a process which comprises: a) preparing an aqueous solution containing a source of casein and a basic amino acid; and b) adding an aqueous solution of a metal selected from a divalent metal, a trivalent metal and combinations thereof to the solution of step a), form an additional aspect of the present invention.

Likewise, the loaded nanoparticles of the invention obtained according to process [2] of the invention, i.e., the nanoparticles comprising a casein matrix, a basic amino acid, a metal selected from a divalent metal, a trivalent metal and combinations thereof, and a BAC, produced by means of a process which comprises: a) mixing (i) an aqueous solution containing a source of casein and a first basic amino acid with (ii) a solution containing a BAC; and b) adding an aqueous solution of a metal selected from a divalent metal, a trivalent metal and combinations thereof to the mixture resulting from step a), form an additional aspect of the present invention.

Applications

The nanoparticles of the invention can be used as technological additives, for example, fat substitutes, etc. They also have the capacity for encapsulating a BAC, e.g., a water soluble BAC or a fat soluble BAC.

In a particular embodiment, the nanoparticles of the invention enable the encapsulation of a BAC, preferably a water soluble BAC, more preferably acidic water soluble BAC, and its incorporation in pharmaceutical, cosmetic and food compositions since other ingredients that are not natural polymers (preventing toxicity associated with synthetic polymers) and not food-grade are not used in the preparation thereof and in the end product (nanoparticles). Said nanoparticles protect the BAC from degradation by external agents (light, pH changes, oxidation, etc.).

Advantageously, the nanoparticles of the invention have a mean size less than 1 µm, preferably comprised between 50 and 200 nm, more preferably about 140 nm, in order to prevent the alteration of organoleptic properties (texture on the palate).

Likewise, the nanoparticles of the invention improve the bioavailability of the BAC in the intestine, protecting said BAC from the peptic acid conditions of the stomach and facilitating their dissolution and release in the intestine.

The nanoparticles of the invention can be resuspended in aqueous medium protecting the BAC from degradation in dissolution. They can further be presented in the form of dry powder, maintaining the BAC in a stable condition and enabling its storage for long periods of time (particularly, for its incorporation in solid food preparations).

Additionally, the nanoparticles of the invention are also suitable for preparing cosmetic and pharmaceutical compositions for topical use.

Therefore, in another aspect, the invention relates to a composition, hereinafter "composition of the invention", comprising at least one nanoparticle of the invention; in a particular embodiment, the nanoparticle of the invention is a nanoparticle comprising a casein matrix, a basic amino acid and a metal selected from a divalent metal, a trivalent metal and combinations thereof; in another particular embodiment, the nanoparticle of the invention is a loaded nanoparticle of the invention, i.e., a nanoparticle comprising a casein matrix, a basic amino acid, a metal selected from a divalent metal, a trivalent metal and combinations thereof, and a BAC with nutritional, therapeutic and/or cosmetic activity, and a pharmaceutically or cosmetically acceptable carrier or a carrier suitable for food.

In a particular embodiment, said BAC is selected from the group consisting of amino acids, antimicrobial agents, aromatizing agents, preservatives, sweeteners, steroids, drugs, hormones, lipids, peptides, polynucleotides, polysaccharides, proteins, proteoglycans, flavoring agents, vitamins, and mixtures thereof.

In a particular embodiment, said BAC is a water soluble BAC, preferably acidic water soluble BAC. Non-limiting illustrative examples of water soluble BACs include vitamins, for example, vitamins of the B or C families and the derivatives, salts or esters thereof; hyaluronic acid, chondroitin sulphate, thioctic acid, the salts or esters thereof, etc. In a particular embodiment, said water soluble BAC is selected from the group consisting of folic acid, 4-aminobenzoic acid, niacin, pantothenic acid, thiamine monophosphate, thiamine pyrophosphate, thiamine triphosphate, ascorbic acid, pteroylpolyglutamic acids (folic acid derivatives: folate polyglutamates; polyglutamate folates), folinic acid, nicotinic acid, hyaluronic acid, thioctic acid, p-coumaric acid, caffeic acid, the pharmaceutically or cosmetically acceptable or food-grade derivatives, esters or salts thereof, and mixtures thereof.

In another particular embodiment, said BAC is a fat soluble BAC. Non-limiting illustrative examples of fat soluble BACs include vitamins, for example of the A, D, E, K families and derivatives thereof, phospholipids, carotenoids (carotenes, lycopene, lutein, capsanthin, zeaxanthin, etc.), omega-3 fatty acids (e.g. DHA, EPA, etc.), amino acids (e.g., iso-leucine, leucine, methionine, phenylalanine, tryptophan, and valine), phytostanols and phytosterols (e.g. sitosterol, campesterol, stigmasterol, etc.), polyphenols (e.g. quercetin, rutin, resveratrol, kaempferol, myricetin, isorhamnetin, etc.) and derivatives thereof.

In a particular embodiment, the composition of the invention is a pharmaceutical composition suitable for its administration by topical route; to that end, said composition comprises a pharmaceutically acceptable carrier which comprises one or more excipients suitable for administration by topical route, for example, in the form of a gel, ointment, cream, etc. Information about excipients suitable for the formulation of pharmaceutical compositions intended for administration by topical route as well as about the production of said pharmaceutical compositions can be found in the book "Tratado de Farmacia Galénica", by C. Faulí i Trillo, 10$^{th}$ Edition, 1993, Luzán 5, S. A. de Ediciones. The dose of nanoparticles of the invention to be administered may vary within a broad range, for example, between approximately 0.5 (g/cm$^2$ of area to be treated) and approximately 2 (g/cm$^2$ of area to be treated) of a composition of the invention containing between 0.1% and 30% of the nanoparticles of the invention, preferably between 0.5% and 5%.

In another particular embodiment, the composition of the invention is a cosmetic composition suitable for administration by topical route; to that end, said composition comprises a cosmetically acceptable carrier comprising one or more excipients suitable for administration by topical route, for example, in the form of a gel, cream, shampoo, lotion, etc. Information about excipients suitable for the formulation of cosmetic compositions intended for administration by topical route as well as about the production of said pharmaceutical compositions can be found in the book "Manual de Cosmetología", by Octavio Díez Sales, 1$^{st}$ Edition, 1998, Editorial Videocinco, S. A.

In another particular embodiment, the composition of the invention is a food composition, such as a solid, liquid or semi-solid food preparation.

In a particular embodiment, the composition of the invention comprises:
casein, between 10% and 50% by weight;
folic acid, between 0.9% and 2.5% by weight;
calcium, between 1% and 6% by weight; and
a basic amino acid, between 1% and 7% by weight; and
a saccharide, between 30% and 80% by weight,
wherein all the proportions are by weight with respect to the total weight of the composition.

In another particular embodiment, the composition of the invention comprises:
casein, between 10% and 50% by weight;
folic acid, between 0.9% and 2.5% by weight;
calcium, between 1% and 6% by weight; and
a basic amino acid, between 1% and 7% by weight;
a saccharide, between 20% and 55% by weight; and
ascorbic acid, between 1% and 25%,
wherein all the proportions are by weight with respect to the total weight of the composition.

Alternatively, the composition of the invention can be incorporated into a foodstuff; therefore, in another aspect, the invention relates to a foodstuff comprising a composition of the invention. Said foodstuff can be found in liquid, semi-solid or solid form. Advantageously, in order to prevent or minimize the total or partial dissolution of the nanoparticles of the invention and thus to contribute to their stability, said foodstuff has an acidic pH, i.e., less than 7, preferably less than or equal to 6, more preferably less than or equal to 5. Illustrative examples of foodstuffs that can be enriched or fortified with the composition of the invention include milk and derivatives thereof (yoghurts, cheeses, curds, etc.), juices, jams, bakery and pastry products, fermented meat, sauces, etc. Similarly, the composition of the invention can be incorporated into an animal food product, for example, in feeds.

EXAMPLES

The following examples describe the production of casein particles that may incorporate a biologically active compound specifically folic acid, inside them. They are capable of protecting the compound from degradations that it may undergo in the food due to the previously mentioned multiple factors. Said examples have also shown the capacity of these nanoparticles to protect folic acid from gastric conditions after the intake thereof and to release it into intestinal medium.

General Process for Producing Empty Casein Nanoparticles

The process for producing casein nanoparticles comprises dissolving sodium caseinate (ANVISA, Madrid, Spain) in an aqueous medium together with a determined amount of basic amino acid followed by adding, under magnetic stirring and with continuous flow, a determined volume of the calcium solution, giving rise to the formation of the nanoparticles with the appearance of a milky suspension.

Physicochemical Characterization of the Nanoparticles

The different studies necessary to achieve a complete physicochemical characterization of the nanoparticles are described below.

The size and the surface charge of the nanoparticles were determined from physicochemical tests, the latter being determined through the measurement of the zeta potential. The first of the parameters was obtained by photon correlation spectroscopy using a Zetasizer nano Z-S (Malvern Instruments/Optilas, Spain), whereas the zeta potential was measured using a Zeta Potential Analyzer (Brookhaven Instruments Corporation, New York, USA).

The yield of the process for forming nanoparticles was calculated through the quantification of the remaining free casein after obtaining the nanoparticles, collected in the supernatants obtained upon centrifuging the formulation (17,000×g, 20 minutes). Thus, the amount of casein that forms particles in the formulation was estimated as the difference between the initial amount added and the amount quantified in the supernatants collected during the step of purification. Said quantification was performed by ultraviolet (UV) spectrometry at 282 nm (Agilent 8453, UV-visible spectroscopy system). The yield was estimated as:

$$\text{Yield}(\%) = [(\text{mg total caseinate} - \text{mg caseinate in supernatant})/\text{mg total caseinate}] \times 100 \quad [\text{Eq. 1}]$$

To perform different calculations, a calibration curve between 150 and 1,500 µg/mL ($R^2$=0.9992; LD=36 µg/mL; LQ=119 µg/mL) was used.

In addition, a study for quantifying the pellet obtained after centrifugation was performed to confirm the results obtained by difference between the total caseinate and the caseinate contained in the supernatant. In this case, 0.05 M NaOH was used to break the particles, this being the same medium used for preparing the calibration curve. Therefore, in this case the yield was estimated as:

$$\text{Yield}(\%) = [(\text{mg caseinate in pellet})/\text{mg total caseinate}] \times 100 \quad [\text{Eq. 2}]$$

The maximum absorbance found for the caseinate prepared in said medium was 300 nm. The concentrations used for constructing the calibration line also ranged between 150 and 1,500 µg/mL ($R^2$=0.9996; LD=26 µg/mL; LQ=85 µg/mL).

The morphology of the nanoparticles was observed by scanning electron microscopy (Zeiss, DSM 940A Germany). To that end, the lyophilized nanoparticles were coated with a 9 nm layer of molecular gold (Emitech K550 Team, Sputter-Coater, United Kingdom) and photographs were taken with a Zeiss DMS 940 A microscope (United States).

General Process for Producing Casein Nanoparticles Containing Folic Acid

The process for producing casein nanoparticles containing folic acid comprises dissolving sodium caseinate in an aqueous medium together with a determined amount of basic amino acid followed by adding, under magnetic stirring, a determined volume of a folic acid solution previously prepared in an aqueous medium with a determined amount of basic amino acid. After incubating the mixture for a few minutes, the last step consists of adding calcium salt, giving rise to the formation of the nanoparticles with the appearance of a milky-yellowish suspension.

Optionally, the formed nanoparticles can be subjected to high pressure hydrostatic treatments (Stansted Fluid Power, ISOLAB Model FPG11500B110; Series No.: 7844) in cycles of between 1 to 5 minutes between 100 and 800 MPa in order to stabilize them.

Then, and after 3 minutes of homogenization by means of stirring, a determined volume of a saccharide solution (lactose, trehalose, mannitol, glucose, sorbitol, maltodextrine or maltose) is added without stopping the stirring. Finally, the suspension is lyophilized or is sprayed in a spray dryer (Buchi Mini Spray Drier B-191, Buchi Labortechnik AG, Switzerland) under the following conditions:

Air inlet temperature: 60-100° C.
Air outlet temperature: 30-90° C.
Air pressure: 2-10 bars [$2\text{-}10\times10^5$ Pa]
Sample pumping rate: 2-9 mL/min
Aspiration: 30-100%
Air flow: 200-900 L/h Optionally, the formulations can be dried after adding the saccharide by means of lyophilization instead of by means of spray drying.

Determination of the Amount of Folic Acid Associated with the Casein Particles

The amount of folic acid associated with the nanoparticles was quantified by high-performance liquid chromatography (HPLC) according to the process described by Faye [Faye Russell, L., Quantitative Determination of Water-Soluble Vitamins. In *Food Analysis by HPLC*, Nollet, L. M. L. (Ed.), Marcel Dekker, Inc., New York, Second Edition, Chapter (2000) pp. 444-445]. The analysis was carried out in a model 1100 LC series chromatograph (Agilent, Waldbornn, Germany) coupled to a diode-array UV detection system. The data was analyzed in a Hewlett-Packard computer by means of Chem-Station G2171 software. For the separation of folic acid, an Alltech C18 Alltima™ column (5 µm, 150 mm×2.1 mm) heated to 40° C. was used with a compatible Gemini® C18 AJO-7596 column. The mobile phase was made up of a mixture of $H_3PO_4$ (33 mM, pH 2.3)/acetonitrile in a gradient (Table 1) and was pumped at a flow of 0.25 mL/min. The detection was performed at 290 nm. The sample injection volume was 10 µL. The folic acid retention time is 22.6±0.5 minutes.

TABLE 1

Gradient conditions for the mobile phase
(A: $H_3PO_4$ 33 mM, B: Acetonitrile)

| Time (min) | A (%) | B (%) |
|---|---|---|
| 0 | 95.0 | 5.0 |
| 8 | 95.0 | 5.0 |
| 33 | 82.5 | 17.5 |
| 45 | 95.0 | 5.0 |

Previously to the quantification of the sample, different calibration lines of concentrations between 2 and 400 µg/mL were prepared, obtaining precise and accurate results greater than 95% with the confirmation that the presence of casein and/or amino acids in the solution would not interfere with the correct quantification of the folic acid.

For fresh sample analysis (before drying them), the supernatants obtained after the filtration of a determined volume of the formulation was quantified through Vivaspin® 300, 000 MWCO dialysis tubes (VIVASPIN 2, Sartorius stedim Biotech, Germany). The pellet was in turn dissolved in 0.05 M NaOH to break the particles and to maintain the casein and folic acid and amino acid in solution and to thus proceed to the quantification thereof. The sum of the folic acid content found in both fractions (supernatant and pellet) coincided at all times with the total initially added. Furthermore, it was also possible to quantify the total folic acid amount by dissolving 1 mL of the formulation in 1 mL of 0.05M NaOH. This study allowed confirming that the differences between the amount of folic acid added and folic acid obtained by quantification through the described chromatography method are greater than 10% in all cases.

In addition, 10 mg of nanoparticles were taken for the quantification of the powdered samples; they were resuspended in 2 mL of water and centrifuged, then proceeding in the same way as with the fresh samples.

Study of the Release Kinetics for the Release of Folic Acid From the Nanoparticles in Simulated Gastrointestinal Medium The release kinetics for the release of folic acid from the nanoparticles were determined by dispersing approximately 10 mg thereof in 2 mL of simulated gastric medium (0 to 2 h) (USP XXIII) at 37±1° C. At determined times the nanoparticle suspensions were centrifuged (17,000×g, 20 minutes) and the amount of folic acid in the supernatants was quantified by the aforementioned HPLC method. After removing the supernatants from the gastric medium, the simulated intestinal medium was added (2 to 24 hours) (USP XXIII) at 37±1° C., then proceeding in the same way as in the case above.

The percentage of folic acid released at all times was calculated taking into account the total content of the vitamin present in the formulation taken for each study.

Pharmacokinetic Studies. Bioavailability of Folic Acid Encapsulated in Casein Nanoparticles The pharmacokinetic studies were carried out according to the rules of the Institution Ethics Committee as well as the European legislation on experimental animals (86/609/EU). To that end, 25 male Wistar rats with a mean weight of 200 g were subjected to normal light-dark (12 hours-12 hours) conditions, and during the week prior to the study they were fed on demand with a folic acid-deficient feed (Folic Acid Deficient Diet. TD. 95247. Harlan, USA) and water. Twelve hours before the administration of the formulations, the rats were isolated in metabolic cages without access to food but with free access to drinking water.

The animals were divided into 5 treatment groups (5 rats per group). Only 1 mL of PBS (phosphate buffer pH 7.4) was administered by oral route to the first group. The following three groups were treated with oral doses of only 1 mg/kg (200 µg/rat) of folic acid incorporated in any of the following formulations: (i) free folic acid (non-encapsulated) (Aditio, Panreac Quimica, Barcelona, Spain); (ii) casein nanoparticles with encapsulated folic acid; (iii) casein nanoparticles treated by high pressure with encapsulated folic acid. 1 mL of each of the different formulations dispersed in water was administered through a gastroesophageal cannula. Finally, the same dose of free folic acid (1 mg/kg) dissolved in saline serum (0.5 mL) was administered to the fifth group by intravenous route into the saphenous vein.

Before administering the formulations, blood was drawn from the saphenous vein of the tail in order to check the basal vitamin level in each rat. After the administration, an approximately 500 µL volume of blood was drawn at different times using serum separator tubes (SARSTEDT Microtube 1.1 mL Z-Gel). In all cases, the blood was drawn after making the animal go to sleep using inhalatory anesthesia (isoflurane:oxygen) to prevent the rats from being in pain, checking their constants at all times.

Subsequently, blood volume was replaced by intraperitoneally administering 500 μL of physiological saline serum previously heated to the temperature of the animal. During this period the condition of the animals was examined (mobility, aggressiveness, allergic reactions and temperature), no significant change being observed.

Pretreatment and Quantification of the Folic Acid of the Serum Samples

The quantification of folic acid in the serum samples obtained after centrifuging the tubes with blood (6,000 rpm, 20 min, 20° C.) was carried out by means of an enzymatic immunoassay technique. To that end, an Elisa Kit (Diagnostic automation, INC. Calabasas, Calif. USA) approved by the FDA for the quantitative determination of folic acid in foods was used. The serum sample was quantified without prior treatment and following the manufacturer's instructions.

Since the kit is designed for use in foods, a series of prior studies was performed in order to confirm its capacity for quantifying the vitamin in serum samples. Said studies consisted of performing an exhaustive comparison between the results obtained by means of the kit and those obtained by the high-performance liquid chromatography method described in previous sections, with the following prior preparation process: Variable amounts (0-300 μL) of folic acid dissolved in a 50 mM solution of sodium tetraborate prepared in 1% (w/v) sodium ascorbate were added to 50 μL of serum. The resulting solution was brought to a final volume of 350 μL (serum dilution 1:7) with the 50 mM solution of sodium tetraborate. Each mixture was brought to boil for 30 minutes and was subsequently cooled to 2° C. and was conserved overnight at said temperature.

After centrifuging the resulting samples at 20,000 rpm for 20 minutes and filtering them through a 20 μm filter, their folic acid content was quantified by means of using the high-performance liquid chromatography method previously described. In this case, and due to the low serum concentration of the vitamin, the standard addition technique was used to minimize errors in the quantification and to remove any matrix interference.

In all the cases studied, the differences in the serum folic acid concentrations of both methods were less than 10%. Therefore, the enzymatic immunoassay technique was chosen to quantify the entirety of the samples since it requires less amount of serum for analysis and is a simpler and faster technique, the limit of detection (2 ng/mL) of which is much less than that of the chromatography technique.

General Process for Producing Casein Nanoparticles Containing a Fat Soluble Active Substance: Quercetin The process for producing casein nanoparticles containing quercetin comprises dissolving sodium caseinate in aqueous medium together with a determined amount of basic amino acid followed by adding, under magnetic stirring, a determined volume of an ascorbic acid solution and subsequently quercetin previously dissolved in ethanol. After incubating the mixture for a few minutes, the last step consists of adding the calcium salt, giving rise to the formation of nanoparticles with an appearance of a milky-yellowish suspension.

Optionally, the formed nanoparticles can be subjected to high pressure hydrostatic treatments (Stansted Fluid Power, ISOLAB Model FPG11500B110; Series No.: 7844) in cycles of between 1 to 5 minutes between 100 and 800 MPa in order to stabilize them.

Then, and after 3 minutes of homogenization by means of stirring, a determined volume of a saccharide solution (lactose, trehalose, mannitol, glucose, sorbitol, maltodextrine or maltose) is added without stopping the stirring. Finally, the suspension is lyophilized, or is sprayed in a spray dryer (Buchi Mini Spray Drier B-191, Buchi Labortechnik AG, Switzerland) under the following conditions:

Air inlet temperature: 60-100° C.
Air outlet temperature: 30-90° C.
Air pressure: 2-10 bars [$2-10 \times 10^5$ Pa]
Sample pumping rate: 2-9 mL/min
Aspiration: 30-100%
Air flow: 200-900 L/h Optionally, after adding the saccharide, the formulations can be dried by means of lyophilization instead of by means of spray drying.

Determining the Amount of Quercetin Associated with the Casein Particles

The amount of quercetin associated with the nanoparticles was quantified by high-performance liquid chromatography (HPLC) according to the process described by Lacopini (Lacopini et al., *J Food Comp Anal* 2008; 21:589-598), although with some variations. The analysis was carried out in a model 1100 LC series chromatograph (Agilent, Waldbornn, Germany) coupled to a diode-array UV detection system. The data was analyzed in a Hewlett-Packard computer by means of Chem-Station G2171 software. For the separation of folic acid, an Alltech C18 Alltima™ column (5 μm, 150 mm×2.1 mm) heated to 40° C. was used with a compatible Gemini® C18 AJO-7596 column and a mixture of water/methanol/glacial acetic acid in a gradient (see Table 2) as mobile phase pumped at a flow of 0.25 mL/min. The detection was performed at 260 nm, the sample injection volume was 10 μL and the quercetin retention time was of 24.2±0.2 minutes.

TABLE 2

Gradient conditions for the mobile phase (A: water, B: methanol, C: glacial acetic acid)

| Time (min) | A (%) | B (%) | C (%) |
|---|---|---|---|
| 0 | 80 | 15 | 5 |
| 15 | 70 | 25 | 5 |
| 20 | 10 | 85 | 5 |
| 30 | 10 | 85 | 5 |
| 35 | 80 | 15 | 5 |
| 40 | 80 | 15 | 5 |

Previously to the quantification of the samples, different calibration lines of concentrations between 1 and 100 μg/mL in hydroalcoholic medium (75% ethanol) were prepared, obtaining precise and accurate results greater than 95%.

For fresh sample analysis (before drying them), the supernatants obtained after the process for the purification of the nanoparticles by filtration (17000 rpm, 20 min) were diluted until obtaining a hydroalcoholic solution with a 50% (w/v) ethanol content.

Finally, the amount of quercetin associated with the nanoparticles [encapsulation efficiency (E.E.)] was calculated as the difference between the amount of quercetin (Q) initially added and the amount thereof quantified in the supernatants according to the following equation:

$$E.E. \ (\%) = \frac{\text{mg total } Q - \text{mg } Q \text{ in supernatant}}{\text{mg total } Q} \cdot 100$$

Example 1

Preparing and Characterizing Empty Casein Nanoparticles. Yield Of the Process for Obtaining them. Influence of the Type of Amino Acid Used on the Stability and Physicochemical Characteristics of the Nanoparticles 1 g of sodium caseinate was dissolved together with 90 mg of lysine in 75 mL of water. Subsequently, 40 mL of 0.8% $CaCl_2$ was added to this solution under magnetic stirring and continuous flow. This process was performed in triplicate.

Figure 2:
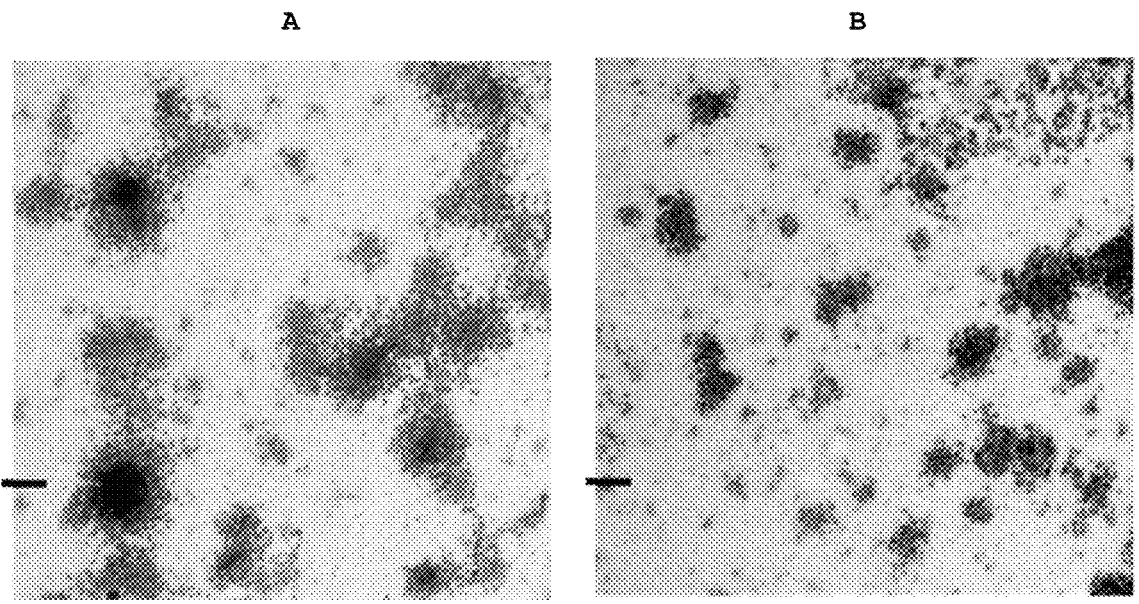
FIG. 2 shows transmission electron microscopy (TEM) images of empty casein nanoparticles. The black bar located in the lower left margin of the images corresponds to a reference of 100 nm.

FIGS. 2 (A and B) shows the images obtained by electron transmission microscopy of the casein particles obtained by this method.

In addition, the same study was performed in the absence of amino acid, or by using 50 mg of arginine instead of lysine, in order to understand the influence of the type of amino acid on the physicochemical characteristics of the particles.

Table 3 summarizes the main physicochemical parameters of the resulting nanoparticles.

TABLE 3

Physicochemical characteristics of the casein nanoparticles (mean ± SD, n = 10). The ratio by weight between the amino acid, lysine or arginine, and the protein is 1:11 and 1:20 respectively

| Formulation | Size (nm) | PDI[a] | Zeta potential (mV) | Yield[b] (%) |
|---|---|---|---|---|
| Casein NP (without amino acid) | 154 ± 30 | 0.24 ± 0.04 | −17.6 ± 0.3 | — |
| Casein NP (lysine) | 138 ± 13 | 0.19 ± 0.02 | −14.0 ± 0.5 | 95 ± 3 |
| Casein NP (arginine) | 157 ± 19 | 0.21 ± 0.03 | −17.5 ± 0.6 | 97 ± 1 |

[a]PDI: polydispersion;
[b]Yield: Percentage of protein transformed into nanoparticles.

The statistical studies performed (non-parametric independent samples test: Kruskal-Wallis) showed that there is no statistically significant evidence to affirm that there are differences between the physicochemical parameters of the formulations. Therefore, it can be concluded that the type of amino acid does not interfere with said characteristics of the empty nanoparticles.

This same study was carried out by varying the ratio of amino acid added to the formulation, similar conclusions being reached, i.e., the ratio and the type of amino acid does not interfere with the final characteristics of the empty particles.

In order to understand the stability of the formulations, the physicochemical parameters of the three types of nanoparticles over time were measured. The results obtained are included in Table 4.

TABLE 4

Physicochemical characteristics of the casein nanoparticles (mean ± SD, n = 6) over time. The ratio by weight between the amino acid, lysine or arginine, and the protein is 1:11 and 1:20 respectively

| Time (hours) | Casein NP (without amino acid) Size | PDI | Casein NP (lysine) Size | PDI | Casein NP (arginine) Size | PDI |
|---|---|---|---|---|---|---|
| 0 | 165 ± 40 | 0.25 ± 0.05 | 138 ± 13 | 0.19 ± 0.02 | 157 ± 21 | 0.21 ± 0.04 |
| 2 | 323 ± 64 | 0.45 ± 0.15 | 155 ± 11 | 0.14 ± 0.02 | 176 ± 21 | 0.16 ± 0.04 |
| 16 | 317 ± 6 | 0.40 ± 0.03 | 157 ± 5 | 0.18 ± 0.03 | 175 ± 21 | 0.14 ± 0.02 |
| 24 | 231 ± 5 | 0.36 ± 0.03 | 155 ± 5 | 0.13 ± 0.02 | 183 ± 4 | 0.25 ± 0.02 |
| 30 | 295 ± 60 | 0.73 ± 0.06 | 157 ± 3 | 0.13 ± 0.02 | 195 ± 4 | 0.32 ± 0.03 |
| 48 | 255 ± 20 | 0.79 ± 0.02 | 157 ± 4 | 0.16 ± 0.01 | 205 ± 3 | 0.33 ± 0.04 |

PDI: polydispersion.

At the time of obtaining them, the three types of nanoparticles had sizes of the same order and relatively low polydispersions (considering that for PDI values less than 0.3 the particle size distribution is homogenous). These size and dispersion values do not show significant variations throughout the entire study in the case of the nanoparticles formulated with amino acid. However, two hours after obtaining them, the nanoparticles that were not formulated with amino acid had a considerable increment both in their mean size and in their polydispersion (for polydispersion values greater than 0.3 the particle size value is not representative, it is only a guideline as there is great heterogeneity in diameters), reaching very high polydispersion values after the end of the study. Said increments are indicative of the existence of phenomena of aggregation between the particles. These phenomena are even confirmed at a macroscopic scale since when the three formulations are observed over time, it was confirmed that the nanoparticles without amino acid precipitate giving rise to the formation of a milky layer, whereas the nanoparticles formulated with amino acid form a homogenous suspension. In view of these results, it is considered that the presence of the amino acid is essential for obtaining particles that are stable over time.

In addition, the three types of formulations were again prepared and their physicochemical characteristics after being dried by means of the spray-drying technique were studied. The conditions of the process were:

Air inlet temperature: 90° C.
Air outlet temperature: 49° C.
Air pressure: 6 bar [6×10$^5$ Pa]
Sample pumping rate: 4.5 mL/min
Aspiration: 100%
Air flow: 600 L/h This study was performed for the purpose of understanding the influence of the amino acid when the nanoparticles are dried at the time of obtaining them since in that instant none of the formulations present phenomena of aggregation. The results obtained are included in Table 5.

TABLE 5

Physicochemical characteristics of the casein nanoparticles (mean ± SD, n = 3) dried by means of spray-drying. The ratio by weight between the amino acid, lysine or arginine, and the protein is 1:11 and 1:20 respectively

| Formulation | Size (nm) | PDI[a] | Zeta potential (mV) |
|---|---|---|---|
| Casein NP (without amino acid) | 305 ± 56 | 0.45 ± 0.02 | −9.8 ± 0.2 |

TABLE 5-continued

Physicochemical characteristics of the casein nanoparticles (mean ± SD, n = 3) dried by means of spray-drying. The ratio by weight between the amino acid, lysine or arginine, and the protein is 1:11 and 1:20 respectively

| Formulation | Size (nm) | PDI$^a$ | Zeta potential (mV) |
|---|---|---|---|
| Casein NP (lysine) | 170 ± 7 | 0.25 ± 0.02 | −11.9 ± 0.9 |
| Casein NP (arginine) | 184 ± 2 | 0.25 ± 0.01 | −9.4 ± 0.2 |

Upon resuspending the nanoparticles with amino acid dried in powder in aqueous medium, it was observed that the size distribution continues to be monodispersed and their sizes are slightly greater than those of their homologues before being dried by spray-drying. However, the nanoparticles formulated without amino acid have greater size and polydispersion values which indicate that they may have undergone phenomena of aggregation during drying. Thus, the presence of amino acid is also necessary when the particles are dried by means of spray-drying.

In view of this, it is concluded that the physicochemical characteristics of the nanoparticles with amino acid differ from those not containing it; they have less aggregation tendency and are therefore the formulations chosen for encapsulating biologically active compounds.

Example 2

Preparing and Characterizing Casein Nanoparticles Containing Folic Acid. Influence of Lysine and Folic Acid Content on Encapsulation Efficiency Different solutions all containing 100 mg of sodium caseinate and variable amounts of lysine (0-8.5 mg) were prepared in a final volume of 7.5 mL of water.

In addition, 300 mg of folic acid were dissolved together with 400 mg of lysine in 50 mL of water.

Subsequently, 1 mL of folic acid solution was added to the caseinate solution. After 5 minutes of incubation, 4 mL of 0.8% $CaCl_2$ were added to the mixture under magnetic stirring and continuous flow. This process was performed in triplicate for each type of formulation.

Figure 3:
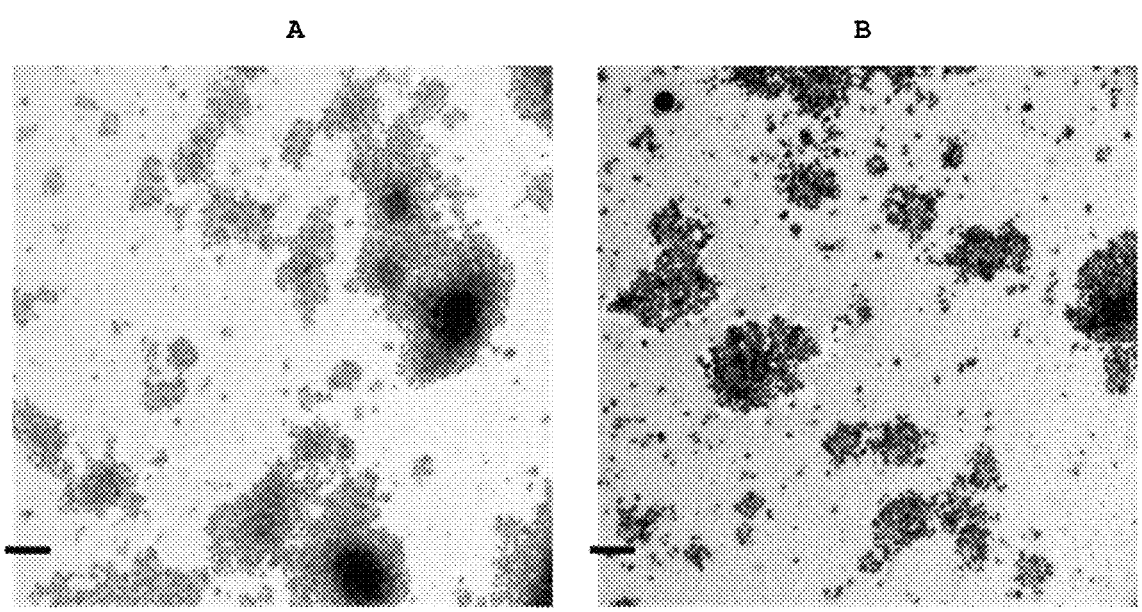
FIG. 3 shows transmission electron microscopy (TEM) images of casein nanoparticles containing folic acid. The black bar located in the lower left margin of the images corresponds to a reference of 100 nm.

FIG. 3 shows the images obtained by electron transmission microscopy of the casein particles with encapsulated folic acid obtained by this method.

The physicochemical characteristics obtained in each case are included in Table 6:

TABLE 6

Physicochemical characteristics of the casein nanoparticles with folic acid and variable amounts of lysine (mean ± SD, n = 6). The ratio by weight between the folic acid and the protein is 1:17

| Ratio by weight lysine:casein$^a$ | Size (nm) | PDI | Zeta potential (mV) | Folic acid content μg FA/mg NP | Encapsulation efficiency |
|---|---|---|---|---|---|
| 0:100 | 159 ± 6 | 0.16 ± 0.04 | −7.9 ± 2.4 | — | — |
| 1:26 | 139 ± 1 | 0.11 ± 0.05 | −17.5 ± 0.5 | 22.1 ± 0.9 | 32.2 ± 0.8 |
| 1:22 | 140 ± 1 | 0.10 ± 0.05 | −16.8 ± 0.7 | 22.3 ± 0.4 | 32.3 ± 0.4 |
| 1:12 | 136 ± 4 | 0.08 ± 0.02 | −16.4 ± 0.7 | 25.7 ± 3.2 | 37.6 ± 4.8 |

$^a$Prior to the addition of folic acid solution
FA: Folic acid; NP: Nanoparticle The statistical studies performed (non-parametric independent samples test: Kruskal-Wallis) showed that there is no statistically significant evidence to consider that there are differences in the physicochemical characteristics of the last three formulations included in the table (with lysine contents of 3.9; 4.5; and 8.5 mg). In the first case, it was confirmed that although the folic acid solution has lysine, the absence of the amino acid in the initial caseinate solution favors the partial precipitation of folic acid with calcium which causes errors in the vitamin quantification as not all the folic acid in the pellet is encapsulated after centrifugation.

Additional studies allowed confirming that when the vitamin solution contains amino acid but the caseinate solution does not, the maximum amount of folic acid that can be incorporated in the formulation without it precipitating is 4 mg, results similar to those in Table 6 (25.5±1 μg FA/mg NP and encapsulation efficiency: 68.7±0.5) then being obtained. Thus, it is confirmed that the presence of amino acid does not influence the amount of encapsulated vitamin. However, since the nanoparticles formulated without amino acid are less stable and have greater aggregation tendency (see Example 1), the formulations were carried out in the presence of such amino acid.

In order to understand the influence of the amount of folic acid added to the formulation on the physicochemical characteristics of the particles, the same study was performed by only varying the amount of folic acid solution added, the amount of amino acid in the initial casein solution in all the cases being constant: 8.5 mg.

Figure 4:
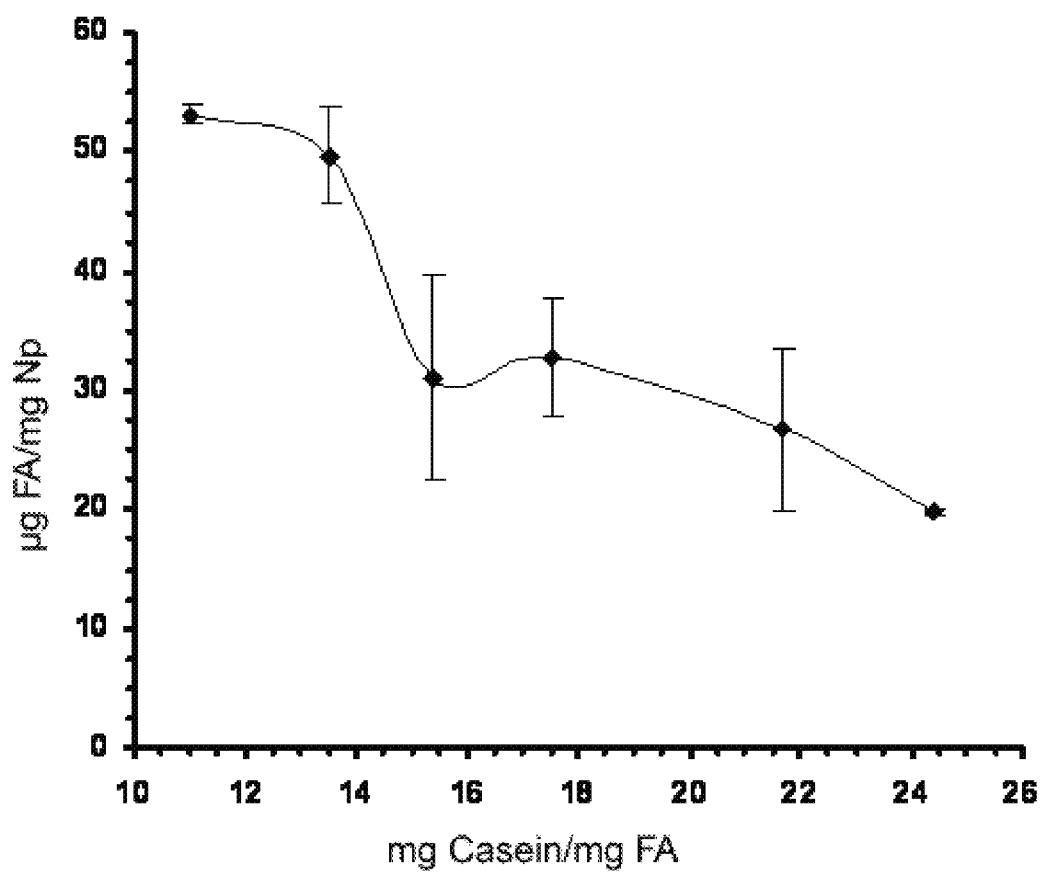
FIG. 4 shows the ratio between the amount of folic acid encapsulated and the amount of casein for each mg of folic acid added to the formulation. In all the formulations the ratio by weight between lysine and the protein, prior to the addition of the folic acid solution, is 1:12.

FIG. 4 shows the ratio between the amount of folic acid encapsulated as a function of the amount of vitamin added to the formulation.

The sizes found in the studied formulations ranged between 132 and 140 nm with a polydispersion less than 0.2 in all cases. In this example, the encapsulation efficiency values are not comparable since the amount of folic acid added to each formulation is different. The maximum value was 73.1±7.5 for a casein:folic acid ratio by weight of 13.5:1.

As a consequence of this study, it can be concluded that as the mg casein/mg FA ratio in the formulation is reduced (i.e., as the initial amount of folic acid added to the formulation increases) an increased amount of folic acid encapsulated inside the nanoparticles is obtained. However, when the amount of casein present in the formulation (in mg) for each mg of folic acid is less than the values experienced, precipitates and unstable formulations such as those which occurred in the absence of lysine are observed.

Example 3

Preparing and Characterizing Casein Nanoparticles Containing Folic Acid Dried by Spray Drying. Influence of the Drying Process on the Final Formulation Two solutions, both containing 1,000 mg of sodium caseinate and 90 mg of lysine were prepared in a final volume of 75 mL of water.

In addition, 600 mg of folic acid were dissolved together with 800 mg of lysine in 100 mL of water.

Subsequently, 7.5 mL of the folic acid solution were added to each caseinate solution. After 5 minutes of incubation 40 mL of 0.8% $CaCl_2$ were added to the mixture under magnetic stirring and continuous flow.

Finally, one of the formulations was centrifuged for the quantification of folic acid in the supernatant and pellet, while 1,900 mg of lactose was added therein to the other before drying it by means of using a spray dryer. The conditions of the process were:

Air inlet temperature: 90° C.
Air outlet temperature: 45° C.
Air pressure: 6 bar [$6 \times 10^5$ Pa]
Sample pumping rate: 4.5 mL/min
Aspiration: 95%
Air flow: 600 L/h The physicochemical characteristics observed in both cases care included in Table 7.

TABLE 7

Physicochemical characteristics of the casein nanoparticles with folic acid quantified in fresh nanoparticles or after drying them by spray dryer (mean ± SD, n = 6). The ratio by weight between the lysine and protein in the final formulation is 1:7, and the ratio between the folic acid and casein is 1:22

| Type of Formulation | Size (nm) | PDI | Zeta potential (mV) | Folic acid content µg FA/mg NP | Encapsulation efficiency |
|---|---|---|---|---|---|
| Spray Drying | 157 ± 5 | 0.17 ± 0.01 | −15.7 ± 0.3 | 18.6 ± 3.4 | 41.4 ± 7.6 |
| Fresh | 137 ± 3 | 0.08 ± 0.02 | −16.7 ± 0.7 | 27.6 ± 0.7 | 58.7 ± 1.4 |

FA: Folic acid; NP: Nanoparticle

The statistical studies performed (non-parametric independent samples test: Kruskal-Wallis) showed that there is a statistically significant difference (p<0.05) between the encapsulation efficiencies obtained for both formulations. This difference may be due to the process for drying the formulation by spray drying at the indicated temperatures causing a partial degradation of the casein nanoparticles, giving rise to a release of part of the previously encapsulated folic acid.

These results show the need to apply a method to crosslink the particles as in doing so their stability can be improved and the aforementioned reduction of the encapsulation efficiency in the process for centrifuging or drying the formulation is prevented.

Example 4

Preparing and Characterizing Casein Nanoparticles with Lysine, Containing Folic Acid Stabilized by High Pressure and Dried by Means of the Spray Drying Technique. Influence of the Treatment on the Physicochemical Characteristics of the Nanoparticles Different solutions, all containing 1,000 mg of sodium caseinate and 90 mg of lysine, were prepared in a final volume of 75 mL of water.

In addition, 600 mg of folic acid were dissolved together with 800 mg of lysine in 100 mL of water.

Subsequently, 7.5 mL of the folic acid solution were added to the caseinate solution. After 5 minutes of incubation, 40 mL of 0.8% $CaCl_2$ were added to the mixture under magnetic stirring and continuous flow.

Once the particles were formed, the formulations were transferred to sealed plastic bags and subjected to high pressure hydrostatic treatment (0 MPa; 100 MPa, 5 minutes; 200 MPa, 5 minutes; 400 MPa, 5 minutes; 600 MPa, 5 min, or 800 MPa, 5 min).

Once the process ended, 1,900 mg of lactose dissolved in water were added to each formulation and the drying thereof was performed using the spray drying technique under the following conditions:

Air inlet temperature: 85° C.
Air outlet temperature: 45° C.
Air pressure: 6 bar [$6 \times 10^5$ Pa]
Sample pumping rate: 4.5 mL/min
Aspiration: 95%
Air flow: 600 L/h Table 8 summarizes the main physicochemical characteristics of the resulting nanoparticles.

TABLE 8

Physicochemical characteristics of the casein nanoparticles with folic acid and different high pressure treatments (mean ± SD, n = 6). The final ratio by weight between the lysine and casein is 1:7, and the ratio between the folic acid and casein is 1:22

| Type of Formulation | Size (nm) | PDI | Zeta potential (mV) | Yield (% by mass) | Folic acid content µg FA/mg NP | Encapsulation efficiency | µg FA/mg formulation |
|---|---|---|---|---|---|---|---|
| Without high pressures | 157 ± 5 | 0.17 ± 0.01 | −15.7 ± 0.3 | 56.4 | 18.6 ± 3.4 | 41.4 ± 7.6 | 12.1 ± 0.4 |
| 100 MPa 5 min | 144 ± 3 | 0.13 ± 0.01 | −13.6 ± 0.2 | 54.1 | 25.3 ± 4.5 | 55.1 ± 7.6 | 11.5 ± 1.4 |
| 200 MPa 5 min | 139 ± 1 | 0.22 ± 0.02 | −13.2 ± 0.5 | 67.6 | 23.2 ± 0.9 | 52.1 ± 2.1 | 11.2 ± 1.4 |
| 400 MPa 5 min | 121 ± 3 | 0.14 ± 0.01 | −13.3 ± 0.5 | 68.2 | 25.5 ± 3.2 | 58.7 ± 4.8 | 11.9 ± 1.4 |
| 600 MPa 5 min | 111 ± 2 | 0.15 ± 0.01 | −12.8 ± 0.4 | 47.7 | 30.8 ± 3.0 | 67.8 ± 5.5 | 11.8 ± 0.9 |
| 800 MPa 5 min | 115 ± 3 | 0.12 ± 0.01 | −14.2 ± 0.8 | — | 31.4 ± 3.5 | 65.8 ± 8.1 | 12.1 ± 1.5 |

FA: Folic acid;
NP: Nanoparticle

As can be observed in Table 8, regardless of the type of treatment applied to the formulations, the nanoparticles have similar surface charges. However, the data allows detecting that as the pressure applied on the treatment increases, the particle size obtained is smaller, reaching a maximum reduction of 7%. However, the amount of encapsulated vitamin (and therefore the encapsulation efficiency) reaches greater values as the applied pressure increases, 65% increments with respect to the formulations without treatment (in the case of the samples treated with 800 MPa) being obtained.

Figure 5:
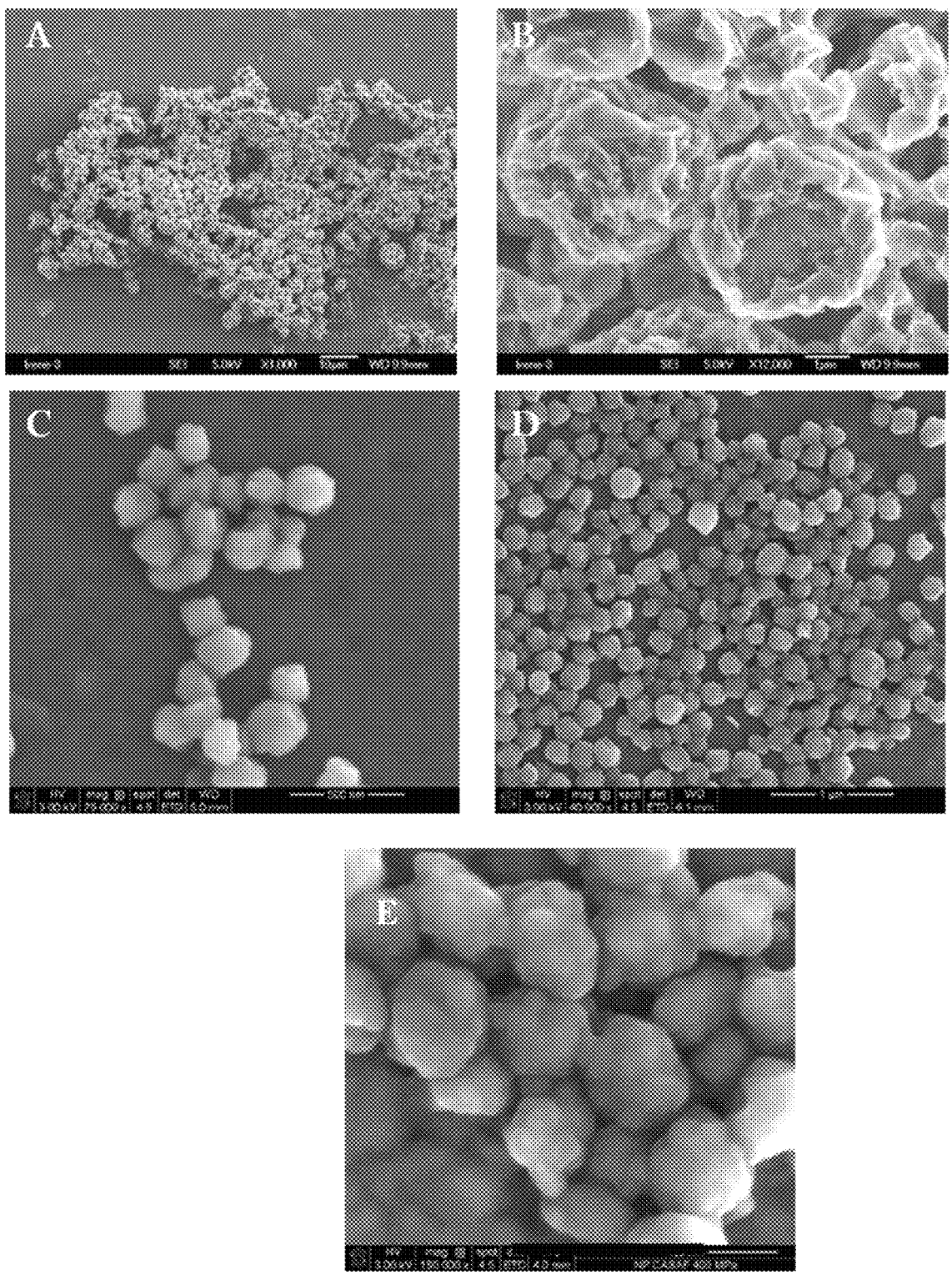
FIG. 5 shows scanning electron microscopy (SEM) micrographs of casein nanoparticles containing folic acid and with lysine in their formulation without high pressure treatment (A and B), with treatment at 100 MPa, 5 minutes (C), with treatment at 400 MPa, 5 minutes (D) and with treatment at 800 MPa, 5 minutes (E).

In addition, FIG. 5 shows the micrographs of the formulations without high pressure treatment and those treated with 100, 400 and 800 MPa obtained by scanning electron microscopy. They show how the nanoparticles without high pressure hydrostatic treatment are partially altered by the different processes to which they have been subjected after being obtained (drying by spray drying, centrifugation, performing micrography in the process of which high temperatures are reached) is confirmed, whereas those that have been subjected to the different high pressure treatments are more stable.

These results show that the high pressure hydrostatic treatments applied cross-links the nanoparticles making them more stable and therefore preventing them from degrading after centrifugation, drying and photographing. All this explains the greater encapsulation efficiencies obtained in the treated samples because the partial degradation of the nanoparticles in some of these processes for drying or centrifugation would entail the release of folic acid and therefore lower encapsulation efficiencies are obtained.

Example 5

Preparing and Characterizing Casein Nanoparticles with Arginine, Containing Folic Acid Using High Pressures, Dried by Spray Drying. Influence of the Amino Acid Used on the Final Result A solution of 3,065 mg of sodium caseinate and 123 mg of arginine was prepared in a final volume of 210 mL of water.

In addition, 605 mg of folic acid were dissolved together with 800 mg of arginine in 100 mL of water.

Subsequently, 27 mL of the folic acid solution were added to the caseinate solution. After 5 minutes of incubation, 120 mL of 0.8% $CaCl_2$ were added to the mixture under magnetic stirring and continuous flow.

Once the particles were formed, the formulation was transferred to a sealed plastic bag and was subjected to a high pressure hydrostatic treatment consisting of a 5 minute cycle at 400 MPa.

Once the process ended, 5,880 mg of mannitol dissolved in water were added therein to 300 mL of the formulation treated by high pressure and the drying thereof was performed using the spray drying technique under the following conditions:

Air inlet temperature: 85° C.
Air outlet temperature: 45° C.
Air pressure: 6 bar [$6 \times 10^5$ Pa]
Sample pumping rate: 4.5 mL/min
Aspiration: 95%
Air flow: 600 L/h The main physicochemical characteristics of the resulting formulation are summarized in Table 9.

TABLE 9

Physicochemical characteristics of the casein nanoparticles with arginine and folic acid treated by high pressure and dried by means of spray drying (mean ± SD, n = 6). The final ratio by weight between the arginine and protein is 1:9, and the ratio between the folic acid and casein is 1:19

| Type of Formulation | Size (nm) | PDI | Zeta potential (mV) | Yield (% by mass) | Folic acid content μg FA/mg NP | Encapsulation efficiency | μg FA/mg Formulation |
|---|---|---|---|---|---|---|---|
| 400 MPa 5 min | 137 ± 6 | 0.20 ± 0.01 | −11.9 ± 0.1 | — | 33.5 ± 2.2 | 59.8 ± 3.9 | 13.9 ± 0.6 |

FA: Folic acid;
NP: Nanoparticle

Figure 6:
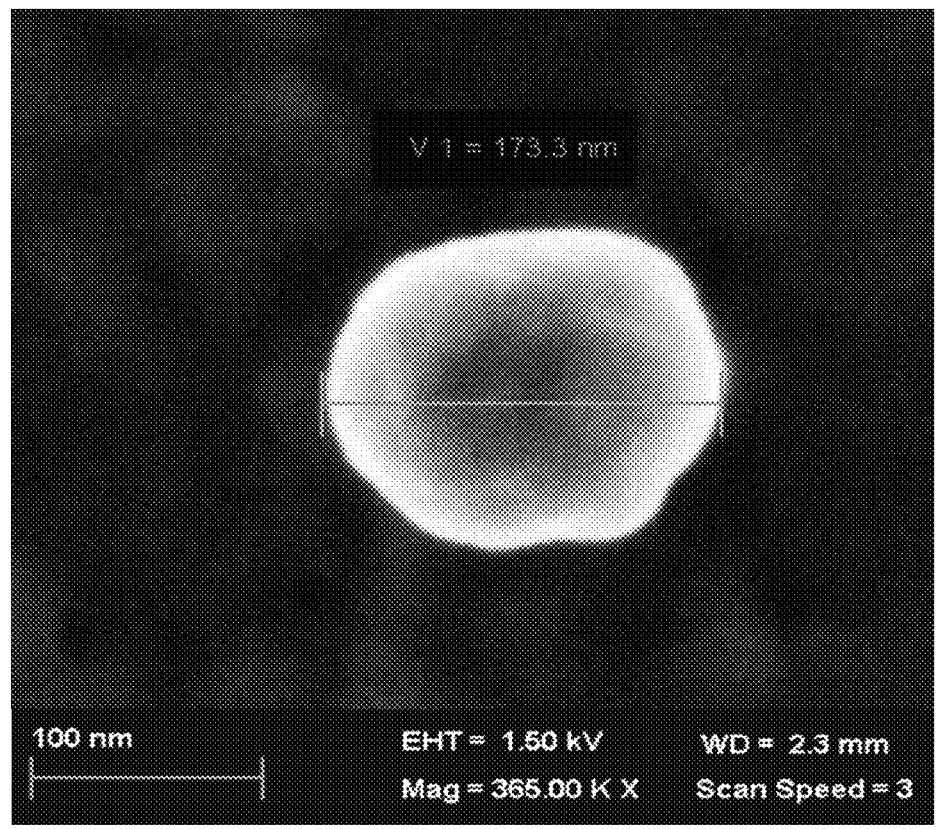
FIG. 6 shows a scanning electron microscopy (SEM) micrograph of casein nanoparticles containing folic acid and with arginine in their formulation with treatment at 400 MPa, 5 minutes.

FIG. 6 shows a scanning electron microscopy (SEM) micrograph of casein nanoparticles containing folic acid and with arginine in their formulation with treatment at 400 MPa, 5 minutes.

As can be seen, the resulting formulation has characteristics similar to the nanoparticles obtained using lysine instead of arginine.

Example 6

Study of the Release Kinetics for the Release of Folic Acid From the Nanoparticles in Simulated Gastrointestinal Medium Influence of the High Pressure Treatment on Release Kinetics In order to perform the release studies, the powder formulations described in Example 4 (without treatment by high pressures, treated at 100 MPa and at 400 MPa) were taken.

Figure 7:
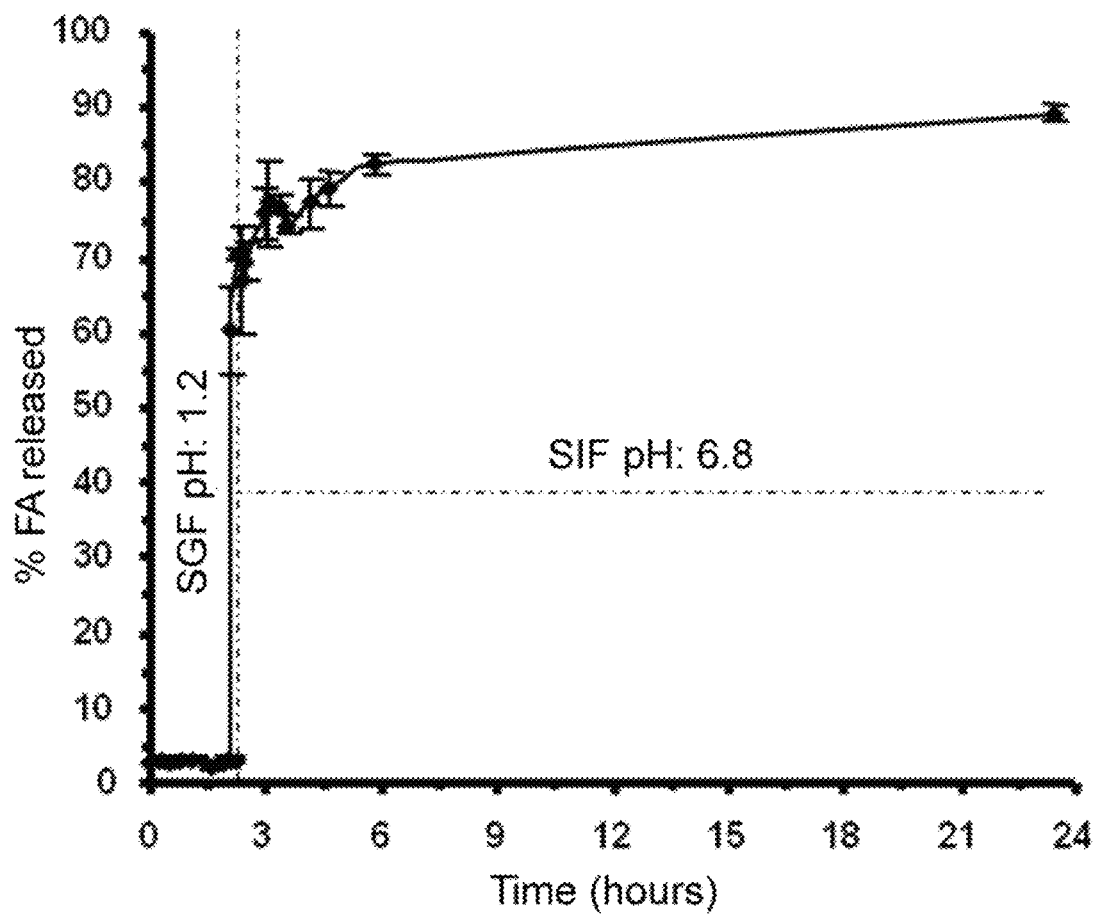
FIG. 7 shows the release of folic acid from the casein nanoparticles without high pressure treatment after their incubation in simulated gastric fluid (SGF) (during the first 2 hours: 0-2 h) and simulated intestinal fluid (SIF) (2 to 24 h) at 37±1° C. The data show the mean±standard deviation (n=6).

FIG. 7 shows the release kinetics obtained for the case of samples without treatment by high pressures. In it, it is seen that after two hours of incubation in gastric medium, maximum folic acid release values of 4% are reached. However, in intestinal conditions, the casein particles were dissolved releasing an increased percentage of the vitamin (reaching up to 90% at the 24 hours of the study). Furthermore, in this medium, the samples centrifuged after their incubation virtually did not have a casein pellet which is evident in their dissolution, and therefore, the release of the vitamin. Thus, it is seen that the designed formulation causes the folic acid to be encapsulated throughout the gastric tract, preventing the stomach conditions from reducing its bioavailability. Furthermore, the nanoparticles were dissolved in the intestine, favoring the release of the vitamin and eliminating any toxicity problem that may arise due to the presence of nanoparticles.

Figure 8:
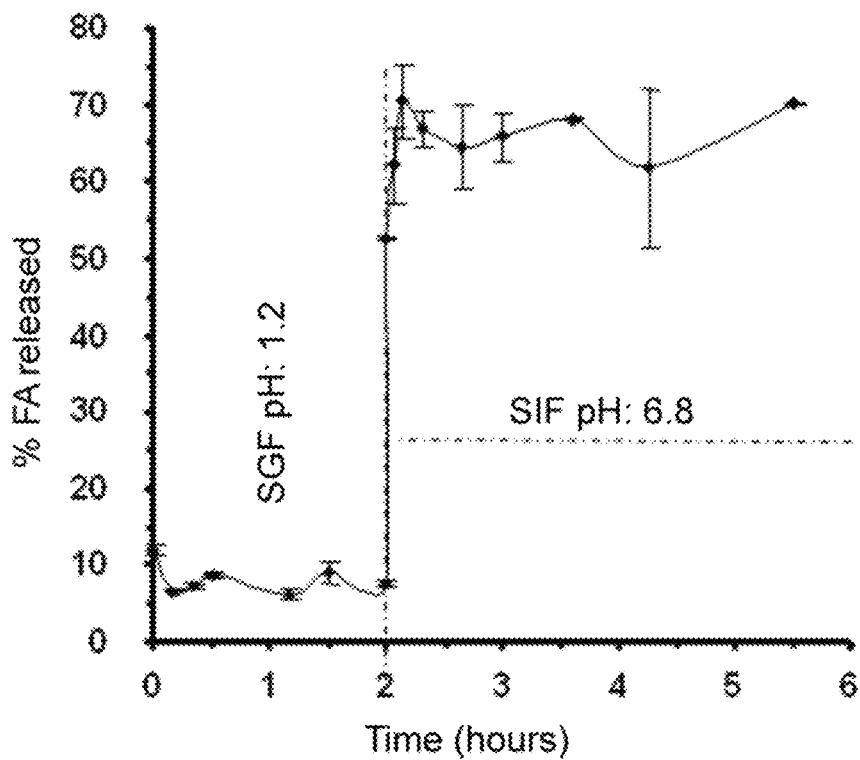
FIG. 8 shows the release of folic acid from the casein nanoparticles with high pressure treatment (A) 150 MPa, 5 minutes and B) 400 MPa, 5 minutes) after their incubation in simulated gastric fluid (SGF) (during the first 2 hours: 0-2 h) and simulated intestinal fluid (SIF) (2 to 8 h) at 37±1° C. The data show the mean±standard deviation (n=4).
Figure 8:
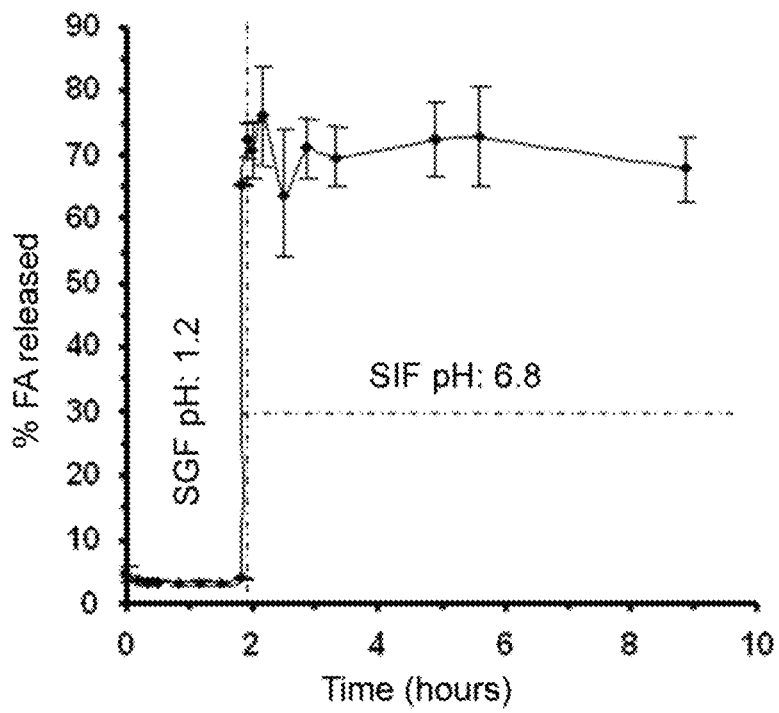

In the case of the samples treated by high pressures, FIGS. 8 (A and B) shows their release kinetics. In them, it can be seen that the profile is very similar to that found for samples without high pressures treatment, the maximum release percentage after 6 hours in simulated intestinal medium being (70%), slightly lower than that found for the samples without treatment at this time (80%).

Thus, applying high hydrostatic pressure to the casein nanoparticles for their cross-linking does not significantly modify the profile of ingredient release from the same although the total amount of the vitamin released after 6 hours reduces by 10%.

Example 7

Pharmacokinetic Study of Folic Acid Encapsulated in Casein Nanoparticles

Table 10 summarizes the main physicochemical characteristics of the nanoparticles tested in the pharmacokinetic study. Both types of nanoparticles (with and without high pressure treatment) were obtained following the process described in Example 5.

TABLE 10

Physicochemical characteristics of the casein nanoparticles with folic acid (mean ± SD, n = 6) used in the pharmacokinetic studies

| Type of Formulation | Size (nm) | PDI | Zeta potential (mV) | Folic acid content μg FA/mg NP |
|---|---|---|---|---|
| Cas NP FA | 134 ± 3 | 0.17 ± 0.02 | −11.8 ± 0.2 | 24.2 ± 1.1 |
| Cas NP FA HP | 134 ± 3 | 0.23 ± 0.03 | −14.4 ± 2.3 | 29.5 ± 1.8 |

FA: Folic acid; NP: Nanoparticle; Cas NP FA: Casein nanoparticles with encapsulated folic acid; Cas NP FA HP: casein nanoparticles with encapsulated folic acid treated with high pressure (400 MPa, 5 min).

The pharmacokinetic study was divided into three phases. The first phase consisted of intravenously administering 1 mg/kg of folic acid dissolved in phosphate buffer; the second phase consisted of orally administering 1 mL of phosphate buffer to the rats from a group of 5 male Wistar rats (the basal vitamin levels over time were studied in this group of rats). Finally, the third phase consisted of orally administering 1 mg/kg of (i) folic acid dissolved in water, (ii) folic acid encapsulated in casein nanoparticles, and (iii) folic acid encapsulated in casein nanoparticles treated by high pressures, to groups of rats made up of 5 animals.

After the administration, an approximately 500 μL volume of blood was drawn at different times (0, 1, 2, 3, 8 and 24 hours) and collected in serum separator tubes, subsequently recovering the blood volume of the animal with a volume equivalent to saline serum by intraperitoneal route. The pharmacokinetic analysis of the data obtained after the administration of folic acid was performed using the process of non-compartmental adjustment of the WiNNonlin 1.5 pharmacokinetic adjustment program (Pharsight Corporation, Mountain View, United States).

Figure 9:
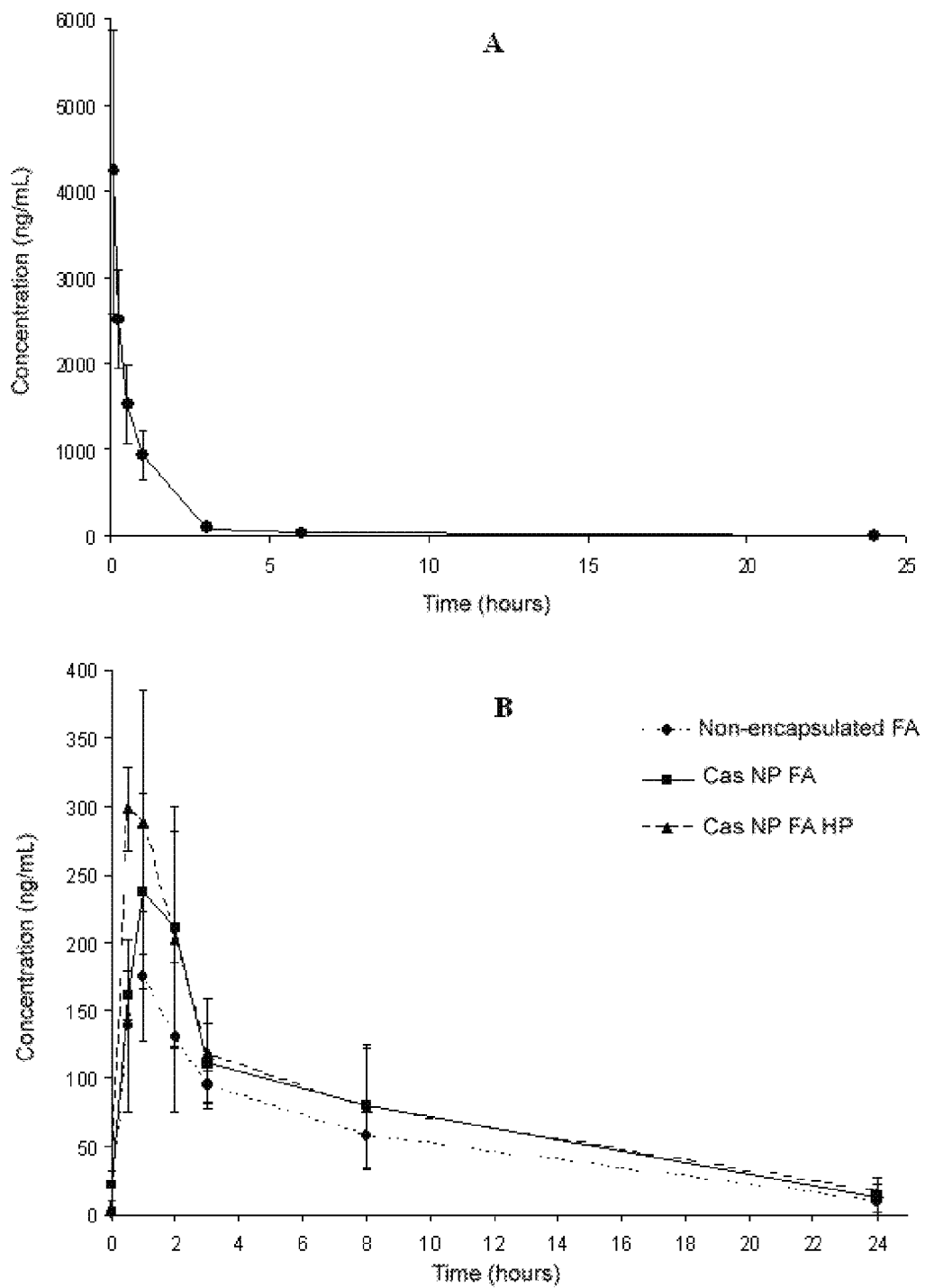
FIG. 9 shows the serum folic acid concentration (ng/mL) as a function of time after the administration of different vitamin formulations in laboratory animals. The results show the mean±standard deviation (n=5).
  A) Intravenous route, dose 1 mg/kg.
  B) Oral route, dose 1 mg/kg: non-encapsulated folic acid dissolved in water (●); folic acid encapsulated in casein nanoparticles dispersed in water (■); folic acid encapsulated in casein nanoparticles treated by high pressures dispersed in water (▲).

The results obtained (after subtracting the basal levels) are collected in FIG. 9. As can be observed, the i.v. administration of the folic acid (FIG. 9A) shows a serum drug concentration peak in the first sample intake followed by a drastic reduction of serum drug levels. The profiles obtained when the vitamin is administered by oral route (FIG. 9B) are different because the concentration maximums are significantly lower; they appear for longer times and decrease in a more gradual manner. However, upon comparing the levels of vitamin found after the oral administration of the folic acid in its free form (without being encapsulated) or encapsulated in casein nanoparticles (with or without high pressure treatment), concentration profiles in similar times were found but the maximum values were greater when encapsulated vitamin was administered.

The values of the pharmacokinetic parameters obtained after performing a non-compartmental analysis of the experimental data of the present study are included in Table 11.

TABLE 11

Pharmacokinetic parameters of the different tested formulations (mean ± SD, n = 5)

| Formulation | $T_{max}$ (min) | $C_{max}$ (ng/mL) | AUC (×10$^4$) (ng × min/mL) | MRT (min) | $F_R$ (%) |
|---|---|---|---|---|---|
| Non-encap FA | 58.8 ± 36.0 | 191.3 ± 41.0 | 7.8 ± 1.5 | 383.8 ± 47.5 | 36.3 ± 7.2 |
| Cas NP FA | 70.0 ± 24.5 | 240.9 ± 71.7 | 11.2 ± 2.8* | 485.8 ± 267.1 | 52.1 ± 13.0* |
| Cas NP FA HP | 52.8 ± 20.8 | 331.3 ± 45.7** | 11.3 ± 2.5* | 560.4 ± 124.7* | 52.7 ± 11.6* |
| IV | — | 4227.1 ± 1651.5** | 21.5 ± 2.8** | 57.8 ± 15.5** | 100** |

*p < 0.05 vs. non-encapsulated folic acid. Mann Whitney U Test.
**p < 0.01 vs. non-encapsulated folic acid. Mann Whitney U Test.
AUC: area under the serum concentration curve
$C_{max}$: maximum concentration
$T_{max}$: time in which $C_{max}$ is reached
MRT: mean residence time
$F_R$: relative bioavailability by percentage.

As can be observed, the AUC values undergo significant variations depending on the type of formulation used. When the vitamin is encapsulated in casein nanoparticles, the AUC values are significantly greater than those after administering the free folic acid and they are furthermore maintained over time up to 24 hours after administration. It was observed that the mean residence time (MRT) of the folic acid in plasma was similar in the two nanoparticle formulations and greater if compared to the free form (oral and i.v.).

According to these results, the oral bioavailability of the casein nanoparticles with encapsulated folic acid, which was 52% in both formulations, 45% greater than those values obtained after the oral administration of the free folic acid by oral route, was calculated.

Example 8

Cosmetic Preparation [1] with Casein Nanoparticles with Encapsulated Folic Acid

A solution containing 200 mg of sodium caseinate and 18 mg of lysine was prepared in a final volume of 15 mL of water.

In addition, 600 mg of folic acid were dissolved together with 800 mg of lysine in 100 mL of water.

Subsequently, 1.5 mL of the folic acid solution were added to the caseinate solution. After 5 minutes of incubation, 8 mL of 0.8% CaCl$_2$ were added to the mixture under magnetic stirring and continuous flow.

Finally, the formulation was centrifuged at 17,000×g, 20 minutes. The supernatant was discarded and the pellet was resuspended in 25 mL of water.

In addition, a solution containing 7 g of glycerin and 0.2 g of sodium nipagin in 42 mL of water was prepared. The solution was heated in a water bath up to 50° C. and subsequently the aqueous solution of casein nanoparticles containing folic acid was added, a final aqueous solution with which the cosmetic formulation will be prepared being obtained.

In addition, 25 g of Neo PCL O/W were also heated at 70° C. until the complete melting thereof. Once this fat phase was melted, the aforementioned aqueous solution was added under constant stirring until obtaining an O/W emulsion that was correct and stable over time. The organoleptic evaluation of the resulting cream was positive, having a homogenous appearance and lacking lumps.

This same study was also performed using the formulation of nanoparticles treated by high pressure (400 MPa, 5 minutes) and dried by a spray dryer described in Example 4. 600 mg of the formulation were taken and resuspended in 25 mL of water, proceeding thereafter in the same way already described above. The resulting cream obtained also had a homogenous appearance and lacked lumps.

Example 9

Cosmetic Preparation [2] with Casein Nanoparticles with Encapsulated Folic Acid

A solution containing 200 mg of sodium caseinate and 18 mg of lysine was prepared in a final volume of 15 mL of water.

In addition, 600 mg of folic acid were dissolved together with 800 mg of lysine in 100 mL of water.

Subsequently, 1.5 mL of the folic acid solution was added to each caseinate solution. After 5 minutes of incubation, 8 mL of 0.8% CaCl$_2$ were added to the mixture under magnetic stirring and continuous flow.

Finally, the formulation was centrifuged at 17,000×g, min. The supernatant was discarded and the pellet was resuspended in 25 mL of water.

In addition, 0.5 g of Carbopol Ultrez 10 was dissolved in 75 mL of water. The suspension of nanoparticles was added to the solution. Once the mixture was homogenized, the sufficient amount of trimethylamine was added until obtaining pH 10. The mixture was homogenized until obtaining a homogenous and stable, slightly yellowish Carbopol gel.

This same test was also performed using the formulation of nanoparticles treated by high pressure (400 MPa, 5 minutes) and dried by spray dryer described in Example 4. 600 mg of the formulation were taken and resuspended in 25 mL of water, proceeding thereafter in the same way already described above. The resulting gel also had a slightly yellowish color and a homogenous and stable appearance.

Example 10

Cosmetic Preparation [3] with Casein Nanoparticles with Encapsulated Folic Acid 3 g of glyceryl monostearate were mixed with 5 g of isopropyl myristate and 2 g of cetyl alcohol. The mixture was heated in a water bath at 70° C.

In addition, 87 g of Carbopol gel containing the casein nanoparticles with folic acid described in Example 8 were heated to 50° C. in a water bath together with 3 g of sorbitol liquid. This solution was added to the former, stirring gently until obtaining a homogenous emulsion.

Example 11

Preparing and Characterizing Casein Nanoparticles Containing Quercetin

A solution containing 100 mg of sodium caseinate and 8.5 mg of lysine (or 5.5 mg of arginine) was prepared in 7.5 mL of water.

TABLE 12

Physicochemical characteristics of the casein nanoparticles with quercetin, amino acid and ascorbic acid (mean ± SD, n = 3). The ratio by weight between the quercetin and protein is 1:67; the ratio by weight between the quercetin and ascorbic acid is 1:3.4

| Formulation | Size (nm) | PDI | Zeta potential (mV) | Quercetin content µg Q/mg NP | Encapsulation efficiency |
|---|---|---|---|---|---|
| Casein NP (lysine) | 115 ± 5 | 0.21 ± 0.03 | −15.5 ± 0.3 | 11.1 ± 0.3 | 86.7 ± 2.6 |
| Casein NP (arginine) | 112 ± 3 | 0.20 ± 0.02 | −17.1 ± 0.3 | 11.7 ± 0.4 | 88.1 ± 2.5 |

Q: Quercetin; NP: Nanoparticle

The results obtained showed that the nanoparticles of the invention are also suitable for encapsulating biologically active compounds with fat soluble characteristics and allow obtaining high encapsulation efficiency percentages.

In addition, the results allow confirming that the presence of one or another amino acid does not influence the physicochemical characteristics of the resulting nanoparticles.

In order to increase the amount of encapsulated quercetin, the study was repeated using lysine as the amino acid and variable amounts of quercetin (between 0.05 and 0.50 mL of the ethanol quercetin solution). The results obtained are included in Table 13.

TABLE 13

Physicochemical characteristics of the casein nanoparticles with lysine, ascorbic acid and variable amounts of quercetin (mean ± SD, n = 3). The ratio by weight between the ascorbic acid and protein (casein) is 1:17

| Ratio by weight quercetin:casein | Size (nm) | PDI | Zeta potential (mV) | Quercetin content µg Q/mg NP | Encapsulation efficiency |
|---|---|---|---|---|---|
| 1:180 | 147 ± 14 | 0.21 ± 0.03 | −17.6 ± 0.3 | 4.3 ± 0.2 | 83.2 ± 4.2 |
| 1:67 | 115 ± 5 | 0.21 ± 0.03 | −15.5 ± 0.3 | 11.1 ± 0.3 | 86.7 ± 2.6 |
| 1:20 | — | — | — | 38.0 ± 1.3 | 89.3 ± 3.1 |

Q: Quercetin; NP: Nanoparticle

In addition, a solution of sodium ascorbate with a concentration of 12 mg/mL was prepared in water, 0.5 mL of which was added to the caseinate and lysine mixture. The reason for using the sodium ascorbate was to prevent quercetin oxidation during the process for obtaining the nanoparticles.

In addition, 50 mg of quercetin was dissolved in 5 mL of ethanol.

Subsequently, 0.15 mL of the quercetin solution was added to the caseinate solution. After 5 minutes of incubation, 4 mL of 0.8% $CaCl_2$ were added to the mixture under magnetic stirring and continuous flow. This process was performed in triplicate for each type of formulation.

The physicochemical characteristics obtained in each case are included in Table 12.

The results obtained show that as the amount of quercetin in the formulation increases, the amount of the encapsulated quercetin increases in the same ratio, while the encapsulation efficiency remains constant.

Additionally, tests following the previously described process were performed but by dispersing the quercetin in water (instead of dissolving them in ethanol) prior to adding them to the caseinate solution. The results obtained shown that part of the quercetin was encapsulated in the casein nanoparticles although the encapsulation efficiency was less than that in the previous case in which the quercetin was dissolved in ethanol prior to the addition thereof to the caseinate solution.

The invention claimed is:
1. A composition comprising at least one nanoparticle and a carrier acceptable for oral administration of food or pharmaceuticals, wherein the nanoparticle comprises a casein matrix, lysine, a biologically active compound, and a metal selected from a divalent metal, a trivalent metal and combinations thereof, wherein the lysine molecules are adhered to the surface of the casein matrix, wherein the biologically active compound is encapsulated in the nanoparticle, and wherein the polydispersion value (PDI) is less than 0.3 over time.

2. The composition according to claim 1, wherein the metal comprises a divalent metal selected from the group consisting of calcium, magnesium, zinc, iron and combinations thereof.

3. The composition according to claim 1, wherein the mean size of the nanoparticles is comprised between 100 and 200 nm.

4. The composition according to claim 1, wherein said nanoparticles are in the form of a dry powder.

5. A foodstuff comprising a composition according to claim 1.

6. The composition according to claim 1, wherein said divalent metal is calcium.

7. The composition according to claim 1, wherein the mean size of the nanoparticles is about 140 nm.

8. The composition according to claim 1, wherein the ratio by weight of lysine to casein is in a range from 1:1 to 1:50.

9. A composition comprising at least one nanoparticle, and a carrier acceptable in food, pharmacy or cosmetics, wherein said nanoparticle comprises a casein matrix, a basic amino acid and a metal selected from a divalent metal, a trivalent metal and combinations thereof, the composition being selected from the group consisting of:
   a composition comprising:
      casein, between 10% and 50% by weight;
      folic acid, between 0.9% and 2.5% by weight;
      calcium, between 1% and 6% by weight;
      a basic amino acid, between 1% and 7% by weight; and
      a saccharide, between 30% and 80% by weight,
   wherein all the proportions are by weight with respect to the total weight of the composition, and
   a composition comprising:
      casein, between 10% and 50% by weight;
      folic acid, between 0.9% and 2.5% by weight;
      calcium, between 1% and 6% by weight; and
      a basic amino acid, between 1% and 7% by weight;
      a saccharide, between 20% and 55% by weight; and
      ascorbic acid, between 1% and 25%,
   wherein all the proportions are by weight with respect to the total weight of the composition.

10. A process for preparing the composition of claim 1, said process comprising combining the at least one nanoparticle with the carrier acceptable for oral administration of food or pharmaceuticals, wherein a method of making said at least one nanoparticle comprises:
   a) mixing (i) an aqueous solution containing a source of casein and the lysine with (ii) a solution containing the biologically active compound; and
   b) adding an aqueous solution of the metal to the mixture of step a), to form a suspension comprising said nanoparticles.

11. The process according to claim 10, which further comprises subjecting the suspension containing the formed nanoparticles to at least one cycle of hydrostatic pressure, at a pressure comprised between 100 and 800 MPa, prior to combination with the carrier acceptable for oral administration of food or pharmaceuticals.

12. The process according to claim 10, which further comprises drying the suspension containing the formed nanoparticles, prior to combination with the carrier acceptable for oral administration of food or pharmaceuticals.

13. The process according to claim 10, wherein said metal comprises a divalent metal selected from the group consisting of calcium, magnesium, zinc, iron and combinations thereof.

14. A process for preparing the composition of claim 1, said process comprising combining the at least one nanoparticle with the carrier acceptable for oral administration of food or pharmaceuticals.

* * * * *